United States Patent
Haruma

(10) Patent No.: US 12,280,045 B2
(45) Date of Patent: Apr. 22, 2025

(54) ANTITUMOR AGENT AND ANTITUMOR EFFECT POTENTIATOR

(71) Applicant: TAIHO PHARMACEUTICAL CO., LTD., Chiyoda-ku (JP)

(72) Inventor: Tomonori Haruma, Ibaraki (JP)

(73) Assignee: TAIHO PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/645,315

(22) PCT Filed: Sep. 6, 2018

(86) PCT No.: PCT/JP2018/033108
§ 371 (c)(1),
(2) Date: Mar. 6, 2020

(87) PCT Pub. No.: WO2019/049956
PCT Pub. Date: Mar. 14, 2019

(65) Prior Publication Data
US 2021/0030738 A1    Feb. 4, 2021

(30) Foreign Application Priority Data

Sep. 8, 2017 (JP) ................. 2017-173352

(51) Int. Cl.
A61K 31/47 (2006.01)
A61K 39/395 (2006.01)
A61P 35/00 (2006.01)

(52) U.S. Cl.
CPC .......... *A61K 31/47* (2013.01); *A61K 39/3955* (2013.01); *A61P 35/00* (2018.01)

(58) Field of Classification Search
CPC .. A61K 31/47; A61K 39/3955; A61K 31/517; A61K 39/395; A61K 45/00; A61K 45/06; A61K 2300/00; A61K 2039/505; A61P 35/00; A61P 37/02; A61P 43/00
See application file for complete search history.

(56) References Cited

U.S. PATENT DOCUMENTS

| | | |
|---|---|---|
| 5,254,541 A | 10/1993 | Kwong |
| 7,135,466 B2 | 11/2006 | Sakai et al. |
| 7,253,286 B2 | 8/2007 | Funahashi et al. |
| 7,425,564 B2 | 9/2008 | Fujiwara et al. |
| 7,579,473 B2 | 8/2009 | Bannen et al. |
| 8,304,427 B2 * | 11/2012 | Suda .............. C07D 405/12 514/312 |
| 9,149,471 B2 | 10/2015 | Miyaura et al. |
| 10,143,688 B2 | 12/2018 | Sato |
| 10,449,189 B2 | 10/2019 | Fujioka |
| 10,695,340 B2 | 6/2020 | Fujioka |
| 11,110,062 B2 * | 9/2021 | Okada ............. A61K 9/2013 |
| 11,191,759 B2 | 12/2021 | Fujioka |
| 2004/0053908 A1 | 3/2004 | Funahashi et al. |
| 2004/0242603 A1 | 12/2004 | Fujiwara et al. |
| 2004/0246603 A1 | 12/2004 | Rydqvist |
| 2005/0113284 A1 | 5/2005 | Nakamura et al. |
| 2006/0160832 A1 | 7/2006 | Funahashi et al. |
| 2006/0247259 A1 | 11/2006 | Funahashi et al. |
| 2007/0191369 A1 | 8/2007 | Lauffer et al. |
| 2008/0161305 A1 | 7/2008 | Forsyth et al. |
| 2008/0312221 A1 | 12/2008 | Fujiwara et al. |
| 2009/0118305 A1 | 5/2009 | Barlaam et al. |
| 2009/0226443 A1 | 9/2009 | Filvaroff et al. |
| 2009/0274693 A1 | 11/2009 | Gilmer et al. |
| 2010/0324087 A1 | 2/2010 | Yamamoto |
| 2010/0063054 A1 | 3/2010 | Bressi et al. |

(Continued)

FOREIGN PATENT DOCUMENTS

| | | |
|---|---|---|
| CN | 1448053 A | 10/2003 |
| CN | A-101491240 | 7/2009 |

(Continued)

OTHER PUBLICATIONS

Miao, et al., Oncotarget 2017, vol. 8, No. 33 p. 53978-53988 (Year: 2017).*
Ott et al., Journal of Clinical Oncology 2017 vol. 35, No. 34, pp. 3823-3829; Published online Aug. 16, 2017 (Year: 2017).*
Overman, et al 2017., Lancet Oncology 2017 18:1182 (Year: 2017).*
Combined Russian Office Action and Search Report issued Feb. 15, 2021 in Russian Patent Application No. 2019125612 (with English translation of the Office Action), 15 pages.
Handbook of Pharmaceutical Excipients, 6th ed. Eds: Rowe, R.C., et al., Pharmaceutical Press and American Pharmacists Association, 2009, 888 pages, p. 211 with cover pages.

(Continued)

*Primary Examiner* — Julie Wu
*Assistant Examiner* — Sydney Van Druff
(74) *Attorney, Agent, or Firm* — Oblon, McClelland, Maier & Neustadt, L.L.P.

(57) ABSTRACT

The present invention is intended to provide a novel antitumor agent that shows marked antitumor effects with reduced side effects. The present invention relates to an antitumor agent characterized by coadministration of an acyl thiourea compound represented by general formula (I) or a salt thereof, and an immune checkpoint molecule regulator.

[Chem. 1]

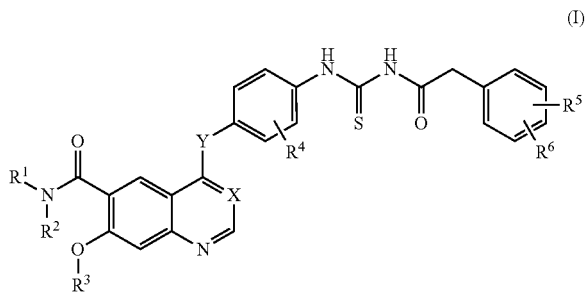

(I)

4 Claims, 2 Drawing Sheets

(56) References Cited

U.S. PATENT DOCUMENTS

| | | |
|---|---|---|
| 2010/0190774 A1 | 7/2010 | Lauffer et al. |
| 2010/0297075 A1 | 11/2010 | Chan et al. |
| 2011/0034439 A1* | 2/2011 | Suda ............... A61P 35/00 |
| | | 514/212.08 |
| 2011/0104161 A1 | 5/2011 | Burgess et al. |
| 2011/0105747 A1 | 5/2011 | Fujiwara et al. |
| 2011/0212967 A1 | 9/2011 | Zhuo et al. |
| 2011/0281865 A1 | 11/2011 | Muthuppalaniappan et al. |
| 2013/0142790 A1 | 6/2013 | Gilmer et al. |
| 2013/0150363 A1 | 6/2013 | Gilmer et al. |
| 2013/0261116 A1 | 10/2013 | Muthuppalaniappan et al. |
| 2013/0345224 A1 | 12/2013 | Zhuo et al. |
| 2014/0256804 A1 | 9/2014 | Iwata et al. |
| 2014/0378409 A1 | 12/2014 | Fujita et al. |
| 2015/0025082 A1 | 1/2015 | Aven et al. |
| 2015/0056207 A1 | 2/2015 | Filvaroff et al. |
| 2015/0133449 A1 | 5/2015 | Muthuppalaniappan et al. |
| 2015/0164879 A1 | 6/2015 | Miyaura et al. |
| 2016/0137650 A1 | 5/2016 | Zhuo et al. |
| 2017/0088626 A1 | 3/2017 | Jure-Kunkel et al. |
| 2017/0360790 A1 | 12/2017 | Patterson et al. |
| 2018/0092901 A1 | 4/2018 | Denker et al. |
| 2018/0161317 A1 | 6/2018 | Sato |
| 2018/0289690 A1 | 10/2018 | Fujioka |
| 2018/0339054 A1 | 11/2018 | Aven et al. |
| 2019/0263923 A1 | 8/2019 | Jure-Kunkel et al. |
| 2020/0060973 A1* | 2/2020 | Okada ............ A61K 9/1694 |
| 2021/0308056 A1* | 10/2021 | Okada ............ A61K 9/1652 |
| 2022/0040313 A1 | 2/2022 | Aven et al. |

FOREIGN PATENT DOCUMENTS

| | | |
|---|---|---|
| CN | A-101926808 | 12/2010 |
| CN | A-105377235 | 3/2016 |
| CN | 106551911 A | 4/2017 |
| EP | 1 411 046 A1 | 4/2004 |
| EP | 1 466 624 A1 | 10/2004 |
| EP | 2 287 155 A1 | 2/2011 |
| JP | 5-238958 A | 9/1993 |
| JP | 2003-238592 A | 8/2003 |
| JP | 2005-272474 A | 10/2005 |
| JP | 2008-504366 T | 2/2008 |
| JP | 2009-518296 A | 5/2009 |
| JP | 2011-500778 A | 1/2011 |
| JP | 2012-4860609 B2 | 1/2012 |
| JP | 2013-518887 A | 5/2013 |
| JP | 2013-529207 A | 7/2013 |
| JP | 2016-196411 A | 11/2016 |
| JP | 2017-507155 A | 3/2017 |
| KR | 10-2004-0030690 A | 4/2004 |
| KR | 10-2010-0132023 A | 12/2010 |
| RU | 2013/2494470 C1 | 9/2013 |
| RU | 2 589 713 C2 | 2/2016 |
| WO | WO 01/47890 A1 | 7/2001 |
| WO | WO 03/000660 A1 | 1/2003 |
| WO | WO 2005/030140 A1 | 4/2005 |
| WO | WO2005-082855 A1 | 9/2005 |
| WO | WO 2005/121125 A1 | 12/2005 |
| WO | WO2006-004636 A2 | 1/2006 |
| WO | WO2006-004833 A2 | 1/2006 |
| WO | WO2006-004884 A2 | 1/2006 |
| WO | WO 2006/104161 A1 | 10/2006 |
| WO | WO 2006/108059 A1 | 10/2006 |
| WO | WO 2007/064797 A2 | 6/2007 |
| WO | WO 2009/053737 A2 | 4/2009 |
| WO | WO 2009/096377 A1 | 8/2009 |
| WO | WO 2009/125597 A1 | 10/2009 |
| WO | WO 2009/137429 A1 | 11/2009 |
| WO | WO 2009/140549 A1 | 11/2009 |
| WO | WO 2010/093789 A2 | 8/2010 |
| WO | WO-A1-2010-150127 | 12/2010 |
| WO | WO 2011/145035 A1 | 11/2011 |
| WO | WO 2011/162835 A1 | 12/2011 |
| WO | WO 2013/058303 A1 | 4/2013 |
| WO | WO 2013/100014 A1 | 7/2013 |
| WO | WO 2015/046484 A1 | 4/2015 |
| WO | WO 2016/090174 A1 | 6/2016 |
| WO | WO 2016/140717 A1 | 9/2016 |
| WO | WO 2016/175305 A1 | 11/2016 |
| WO | WO2016-208744 A1 | 12/2016 |
| WO | WO2018-151177 A1 | 8/2018 |

OTHER PUBLICATIONS

Arun, R., et al., "Cyclodextrins as Drug Carrier Molecule: A Review", Scientia Pharmaceutica, 2008, vol. 76., pp. 567-598 URL: https://www.mdpi.com/2218-.

Jantarat, C., et al., "Curcumin-Hydroxypropyl-β-Cyclodextrin Inclusion Complex Preparation Methods: Effect of Common Solvent Evaporation, Freeze Drying, and pH Shift on Solubility and Stability of Curcumin", Trop J Pharm Res., 2014, vol. 13(8), pp. 1215-1223.

Alonso. E.C.P., et al., "Development of carvedilol-cyclodextrin inclusion complexes using fluid-bed granulation: a novel solid-state complexation alternative with technological advantages", J Pharm Pharmacol., 2016, vol. 68(10) pp. 1299-1309.

Stringer J.L. Drug, in: Encyclopedia Britannica//website, URL: https://www.britannica.com/science/drug-chemical-agent.

Extended European Search Report issued Apr. 30, 2021 in European Patent Application No. 18854415.9, 11 pages.

Jin Zhang, et al., "Recent advances in the development of dual VEGFR and c-Met small molecule inhibitors as anticancer drugs," European Journal of Medicinal Chemistry, vol. 108, XP029383501, 2016, pp. 495-504.

Office Action mailed on Nov. 4, 2020 in co-pending U.S. Appl. No. 16/485,971, 17 pages.

U.S. Appl. No. 15/574,060, filed Nov. 14, 2017, US 2018-0289690 A1, Akio Fujioka.

U.S. Appl. No. 12/937,312, filed Oct. 11, 2010, US 2011-0034439 A1, Yoshimitsu Suda et al.

U.S. Appl. No. 15/570,021, filed Oct. 27, 2017, US 2018-0161317 A1, Ayako Sato.

U.S. Appl. No. 14/369,060, filed Jun. 26, 2014, US 2014-0378409 A1, Hidenori Fujita.

U.S. Appl. No. 16/485,971, filed Aug. 14, 2019, US 2020-0060973 A1, Shinji Okada.

International Search Report and Written Opinion issued on Dec. 4, 2018, in PCT/JP2018/033108, 36 pages (with English translation).

PLoS ONE, "High Potency VEGFRs/MET/FMS Triple Blockade by TAS-115 Concomitantly Suppresses Tumor Progression and Bone Destruction in Tumor-Induced Bone Disease Model with Lung Carcinoma Cells", 11 (10): e0164830 (2016), 21 pages.

Cancer Cell, "Targeting Tumor-Associated Macrophages with Anti-CSF-1R Antibody Reveals a Strategy for Cancer Therapy" 25: 846-859 (2014), 14 pages.

Frontiers in Immunology, "Functional relationship between tumor-associated macrophages and macrophage colony- stimulating factor as contributors to cancer progression", 5: Article 489 (2014), 15 pages.

Cancers, "The Role of TAM Family Receptors in Immune Cell Function: Implications for Cancer Therapy", 8 (10), 97: 8100097 (2016), 22 pages.

Cancers, "The Receptor Tyrosine Kinase AXL in Cancer Progression", 8 (11), 103: 8110103 (2016), 16 pages.

Nat. Rev. Cancer, "The blockade of immune checkpoints in cancer immunotherapy", 12 (4): 252-264 (2012), 31 pages.

The New England Journal of Medicine, "Safety, Activity, and Immune Correlate of Anti-PD-1 Antibody in Cancer", 366; 26: 2443-2454 (2012), 12 pages.

Cell, "Primary, Adaptive, and Acquired Resistance to Cancer Immunotherapy", 168 (4): 707-723 (2017), 17 pages.

Science Translational Medicine, "In vivo imaging reveals a tumor-associated macrophage-mediated resistance pathway in anti-PD-1 therapy", 9 (389): eaal 3604 (2017), 11 pages.

International Search Report issued on May 1, 2018 in PCT/JP2018/005140, (with English translation), 5 pages.

(56) References Cited

OTHER PUBLICATIONS

Opinion of the International Searching Authority issued on May 1, 2018 in PCT/JP2018/005140, (with English translation), 11 pages.
Amin, A. et al., "Nivolumab (anti-PD-1 ; BMS-936558, ON0-4538) in combination with sunitinib or pazopanib in patients (pts) with metastatic renal cell carcinoma (mRCC)", Journal of Clinical Oncology, Jan. 2017, vol. 32, No. 15 supply (May 2014), 3 pages.
Fujita, H, et al, "The Novel VEGF Receptor/MET-Targeted Kinase Inhibitor TAS-115 Has Marked In Vivo Antitumor Properties and a Favorable Tolerability Profile", Molecular Cancer Therapeutics, 2013, vol. 12, No. 12, pp. 2685-2696.
Manegold, C. et al., "The Potential of Combined Immunotherapy and Antiangiogenesis for the Synergistic Treatment of Advanced NSCLC", Journal of Thoracic Oncology, Feb. 2017, vol. 12, No. 2, pp. 194-207.
Lee, C-H. et al., "A phase 1b/2 trial of lenvatinib plus pembrolizumab in patients with renal cell carcinoma.", Annals of Oncology, Aug. 31, 2017, vol. 28, Supply. 5, pp. v295-v296.
Kato Yu, "Combination mechanism of Lenvatinib with immune checkpoint inhibitor by cancer immunity regulation", Japanese Society of Hepato-Biliary-Pancreatic Surgery, Aug. 2017, vol. 75, No. 2, pp. 473-477 (with English abstract).
Kato, Y. et al., "Lenvatinib mesilate (LEN) enhanced antitumor activity of a PD-1 blockade agent by potentiating Th1 immune response.", Annals of Oncology, 2016, vol. 27, Supply. 6, Abstract No. 2PD., ISSN 1569-8041.
Nadal, R. et al., "Final results of a . . . in patients (pts) with metastatic urothelial carcirma (mUC) and other genitourinary (GU) malignancies.", Annals of Oncology, Aug. 31, 2017, vol. 28, supply 5, p. v295.
Davare, M. A. et al., "Structural Insight into selectivity and resistance profiles of ROS1 tyrosine kinase inhibitors", PNAS, 2015, vol. 112, No. 39, pp. E5381-E5390.
Bentzien, F. et al., "In Vitro and In Vivo Activity of Cabozantinib (XL184), an Inhibitor of RET, MET, and VEGFR2, in a Model of Medullary Thyroid Cancer", Thyroid, 2013, vol. 23, No. 12, pp. 1569-1577.
International Search Report issued Jun. 28, 2016, in PCT/JP2016/063413, 2 pages.
Office Action mailed on Mar. 28, 2018 in co-pending U.S. Appl. No. 15/570,021, 6 pages.
Notice of Allowance mailed on Jul. 26, 2018 in co-pending U.S. Appl. No. 15/570,021, 6 pages.
International Search Report issued on May 19, 2009 in PCT/JP2009/01655, 2 pages.
Extended European Search Report issued on Apr. 11, 2012 in Patent Application No. 09730440.6, 5 pages.
Notice of Allowance mailed on Aug. 13, 2012 in co-pending U.S. Appl. No. 12/937,312, 9 pages.
International Search Report Issued Feb. 12, 2013 in PCT/JP2012/083794, 3 pages.
Written Opinion of the International Searching Authority issued Feb. 12, 2013 in PCT/JP2012/083794 filed Dec. 27, 2012, 8 pages.
Office Action mailed on Sep. 24, 2015 in co-pending U.S. Appl. No. 14/369,060, 17 pages.
Extended European Search Report issued on Apr. 28, 2015 in Patent Application No. 12863476.3, 8 pages.
Office Action mailed on Apr. 22, 2016 in co-pending U.S. Appl. No. 14/369,060, 25 pages.
Office Action mailed on Apr. 21, 2017 in co-pending U.S. Appl. No. 14/369,060, 29 pages.
Office Action mailed on Nov. 30, 2017 in co-pending U.S. Appl. No. 14/369,060, 17 pages.
Office Action mailed on Aug. 21, 2019 in co-pending U.S. Appl. No. 14/369,060, 19 pages.
International Search Report issued Sep. 13, 2016 in PCT/JP2016/068902, 3 pages.
Office Action mailed on Sep. 20, 2018 in co-pending U.S. Appl. No. 15/574,060, 8 pages.
Extended European Search Report issued Jan. 30, 2019 in Patent Application No. 16814513.4, 8 pages.
Notice of Allowance mailed on Jun. 17, 2019 in co-pending U.S. Appl. No. 15/574,060, 8 pages.
"Poster Session—Met, Ret and Notch", European Journal of Cancer, vol. 48, No. 6, Nov. 8, 2012, p. 94.
Masako Yokoo, et al., "2-Hydroxypropyl-(3-Cyclodextrin Acts as a Novel Anticancer Agent", PLOS ONE, vol. 10, No. 11, Nov. 4, 2015, pp. 1-20.
Chisa Imamura, "Applied Technology of Cyclodextrin Popular Edition", CMC Publishing Co., Ltd., 2013, pp. 253-261 (with partial English translation).
Kazuhide Ashizawa, et al. "Polymorphic Phenomena of Drug and Science of Crystallization Development and Production and trend of Regulation", Iyakuhin no Takei Gensho to Shoseki no Kagaku, 2002, 77 pages. (with English translation).
Mino R. Caira, "Crystalline Polymorphism of Organic Compounds", Topics in Current Chemistry, vol. 198, 1998, pp. 163-208.
Bradley D. Anderson, et al., "Preparation of Water-Soluble Organic Compounds Through Salt Formation", (Edited by Wermuth, C.G), Saishin Soyaku Kagaku Last Volume, 1999, 65 pages (with English translation).
Seto, T., "Trend of Molecular Target Therapy—from ASCO 201 O ASCO Report: Ling Cancer". Cancer Molecular Target Therapy, vol. 8, No. 4, pp. 267-270, 2010 (with Partial English translation).
Stephen M. Berge et al., "Pharmaceutical Salts", Journal of Pharmaceutical Sciences, vol. 66, No. 1, Jan. 1977, pp. 1-19.
James G. Christensen, et al., "c-Met as a Target for Human Cancer and Characterization of Inhibitors for Therapeutic El Intervention", Cancer Letters, vol. 225, 2005, pp. 1-26.
K. Michael Weidner, et al., "Scatter Factor: Molecular Characteristics and Effect on the Invasiveness of Epithelial Cells", the EJ Journal of Cell Biology, vol. 111, Nov. 1990, pp. 2097-2108.
Paolo M. Cornoglio, et al., "Scatter Factors and Invasive Growth", Cancer Biology, vol. 11, 2001, pp. 153-165.
Xiaohua Xin, et al., "Hepatocyte Growth Factor Enhances Vascular Endothelial Growth Factor-Induced Angiogenesis in Vitro EL and in Vivo", American Journal Of Pathology, vol. 158, No. 3, Mar. 2001, pp. 1111-1120.
Eiji Ichimura, et al., "Expression of c-met/HGF Receptor in Human Non-small Cell Lung Carcinomas in vitro and in vivo and EM Its Prognostic Significance", JPN J. Cancer Res, vol. 87, Oct. 1996, pp. 1063-1069.
Masakazu Nakajima, et al., "The Prognostic Significance of Amplification and Overexpression of c-met and c-erb B-2 in EN Human Gastric Carcinomas", Cancer, vol. 85, No. 9, May 1, 1999, pp. 1894-1902.
Wilfredo Hernandez, et al., "Synthesis, Characterization and Antitumor Activity of Copper (II) Complexes, [Cul$_2$] [HL $_{13}$=N,NEO Diethyl-N'-(R-Benzoyl) Thiourea (R=H, o-Cl and p-NO$_2$)]", Bioinorganic Chemistry and Applications, vol. 3, Nos. 3-4, 2005, pp. 299-316.
Xiao-Ping Rao, et al., "Synthesis and Antitumor Activities of Unsymmetrically Disubstituted Acylthioureas Fused with EP Hydrophenanthrene Structure", Medicinal Chemistry Research, vol. 20, 2011, pp. 333-338.
Takahumi Nishii, et al., "c-Met Inhibitors Intensify the Sensitivity to Anticancer Agents of Gastric Cancer Stem Cell-Like SP EQ Cells", Journal of Japan Society for Cancer Therapy, vol. 43, No. 2, 2008, p. 390, (with Partial English translation).
Sheng-Hua Chu, et al., "c-Met Antisense Oligodeoxynucleotides Increase Sensitivity of Human Glioma Cells to Paclitaxel", Oncology Reports, vol. 24, No. 1, XP 009183704, Jul. 1, 2010, pp. 189-194.
Isaiah J. Fidler, "Tumor Heterogeneity and the Biology of Cancer Invasion and Metastasis" Cancer Research, vol. 38, Sep. 1978, pp. 2651-2660.
"Benign Tumors" Healthline Website, www.healthline.com/health/benign#overview1, Accessed Mar. 29, 2017, 6 pages.
Stephen Neidle, "Cancer Drug Design and Discovery" Elsevier/Academic Press, 2008, pp. 427-431.

(56) References Cited

OTHER PUBLICATIONS

P. Spagnolo, et al., "Idiopathic Pulmonary Fibrosis: Recent Advances on Pharmacological Therapy" Pharmacology & Therapeutics, 2015, 10 Pages.
Richard Hubbard, et al., "Lung Cancer and Cryptogenic Fibrosing Alveolitis, A Population-Based Cohort Study" American Journal of Respiratory and Critical Care Medicine, vol. 161, 2000, pp. 5-8.
David M. Spain, "The Association of Terminal Bronchiolar Carcinoma with Chronic Interstitial Inflammation and Fibrosis of the Lungs" Am Rev Tuberc, 1957, pp. 559-567.
Arnab Datta, et al., "Novel Therapeutic Approaches for Pulmonary Fibrosis" British Journal of Pharmacology, vol. 163,2011, pp. 141-172.
Lu Zhao, et al. "Paracrine Activation of MET Promotes Peritoneal Carcinomatosis in Scirrhous Gastric Cancer" Cancer Science, vol. 104, No. 12, XP002787868, Dec. 2013, pp. 1640-1646.
Yano, S. et al., "Resistance to EGFR-TK Inhibitors Induced by HGF/MET Signaling", Respiratory Medicine, vol. 17, No. 3, pp. 283-288, 201 O ( with Partial English translation).
Korean Office Action issued Nov. 4, 2021 in Korean Patent Application No. 10-2020-7006381 (with English translation), 15 pages.
Office Action issued in corresponding Chinese Appln. 201880012000.X issued on Jan. 25, 2022 (with partial English machine Translation).
Biochemistry (No. 2016-2-013) (for food and related specialties), Thrones, pp. 32-33, China Light Industry Press, Jan. 2017—ISBN 978-7-5184-1040-8 (with English Translation).
"Study on inclusion complexation of insoluble drugs with β-cyclodextrin and its derivatives", Series I, Excellent High Paper of China, Full Database Engineering Technology, Part I (with English Translation).
Office Action issued in corresponding Russian Appln 2020109716 issued on Feb. 15, 2022 (with English Translation).
M.D.Mashkovskiy. Lekarstvennye sredstva (Medicinal Agents), 14th edition, vol. 1, Moscow, 2001, p. 11 (with partial English translation).
U.S. Pat. No. 8,304,427 B2, Nov. 6, 2012, Yoshimitsu Suda, et al.
U.S. Pat. No. 10,449,189 B2, Oct. 22, 2019, Akio Fujioka.
U.S. Pat. No. 10,143,688 B2, Dec. 4, 2018, Ayako Sato.
U.S. Appl. No. 14/369,060, filed Jun. 26, 2014, US 2014/0378409 A1, Hidenori Fujita, et al.
U.S. Pat. No. 11,110,062 B2, Sep. 7, 2021, Shinji Okada.
U.S. Appl. No. 17/347,989, filed Jun. 15, 2021, US 2021/0308056 A1, Shinji Okada.
U.S. Appl. No. 16/645,315, filed Mar. 6, 2020, US 2021-0030738 A1, Tomonori Haruma.
Lu Zhao, et al. "Paracrine Activation of MET Promotes Peritoneal Carcinomatosis 1n Scirrhous Gastric Cancer" Cancer Science, vol. 104, No. 12, XP002787868, Dec. 2013, pp. 1640-1646.
Shukuya, T. et al. "Paradigm Shift from Non-Selective Treatment to Selective Treatment", Mebio Oncology, vol. 6, No. 1, pp. 23-31, 2009 (with Partial English translation).
Uenaka, T. et al "2. Current Status of Development of Molecular Therapeutic drugs Targeting HGF/c-Met", Experimental Medicine, vol. 29, No. 2, pp. 303-309, 2011 (with Partial English translation).
Yano, S. et al., "Resistance to EGFR-TK Inhibitors Induced by HGF/MET Signaling", Respiratory Medicine, vol. 17, No. 3, pp. 283-288, 2010 (with Partial English translation).
"Osteoporosis Prevention, Diagnosis and Therapy", JAMA vol. 285, No. 6, pp. 785-794, Feb. 14, 2001.
T.D. Rachner et al., "Osteoporosis: now and the future", www.thelancet.com vol. 377, Apr. 9, 2011, pp. 1276-1287.
M. Shiraki et al., Long-Term Treatment of Postmenopausal Osteoporosis with Active Vitamin 03, 1-Alpha-Hydroxycholecalciferol (1α-OHD$_3$) and 1, 24 Dihydroxycholecalciferol (1, 24 (OH)2D3, Endocrinol, Japan 1985, 32 (2) 305-315.
R. Rizzoli et al., "Adverse Reaction and Drug-Drug Interactions in the Management of Woman with Postmenopausal Osteoporosis", Calcif Tissue Int (2011), 89:91-104.

"Risks and Benefits of Estrogen Plus Progestin in Healthy Postmenopausal Women", JAMA. Jul. 17, 2002—vol. 288, No. 3, pp. 321-333.
M.A. Bolognese. "SERMs and SERMs with estrogen for postmenopausal osteoporosis", Rev. Endocr Metab Disord (2010) 11 :253-259.
V Lim et al., "New therapeutic targets for osteoporosis: Beyond denosumab", Maturitas 73 (2012), 269-272.
S. Das et al, "Osteoporosis—a current view of pharmacological prevention and treatment", Drug Design. Development and Therapy, 2013:7, pp. 435-448.
E. Canalis, "New Treatment Modalities in Osteoporosis", Endocrine Practice, vol. 16. No. 5, Sep./Oct. 2010, pp. 855-863.
Combined Russian Federation Office Action and Search Report issued on Nov. 29, 2019 in Patent Application No. 201714-5271 /04(077515) (with English translation).
Notice of Reasons for Refusal issued Jan. 26, 2021 in Japanese Patent Application No. 2017-525457 (with English language translation).
Hidenori Fujita, et al., "The Novel VEGF Receptor/MET-Targeted Kinase Inhibitor TAS-115 Has Marked In Vivo Antitumor Properties and a Favorable Tolerability Profile," Molecular Cancer Therapeutics, vol. 12, No. 12, Dec. 2013, 13 pages.
Takafumi Nishii, et al., "c-Met Inhibitor Might be a Promising Molecular-Targeted Molecule Against for CPT11-Resistant Cancer Stem Cells", AACR Annual Meeting, XP 055182601, 2009, 2 pages.
Office Action issued Jan. 28. 2021 in corresponding Korean Patent Application No. 10-2019-7023592 (with English Translation), 10 pages.
Kyu Hyun Choi et al., "Hyaluronic acid gel formulation containing Piroxicam: Hydroxypropyl-β-cyclodextrin inclusion complex for intra-articular delivery" (with English abstract), Biomaterials Research 13 (1) : 1-6(2009), 6 pages.
George SJ et al., "Studies on the Preparation, Characterization, and Solubility of 2-HP-β-Cyclodextrin-Meclizine HCl Inclusion Complexes", Journal of Young Pharmacists vol. 4 / No. 4, (2012). pp. 220-227.
Office Action issued in corresponding Russian Application No. 2019125612 on Feb. 15, 2021 (with English Translation).
Office Action issued in corresponding Russian Application 2019125612 on Jul. 6, 2021, with English Translation.
Stringer J.L. Drug, in: Encyclopedia Britannica//website, URL: hllps://www.britannica.com/science/drug-chemical-agent.
The Pursuit of Responsible Use of Medicines. Sharing and Learning from Country Experiences. Oct. 2, 2012, Technical document. WHO Reference WHO/EMP/MAR/2012.3. URL: https://www.who.int/publications/i/item/WHO-EMP-MAR-2012.3.
Notification of Reason for Refusal issued Nov. 4, 2021 in Korean Patent Application No. 10-2020-7006381 (with English language translation), 15 pages.
Office Action mailed Sep. 30, 2021 in co-pending U.S. Appl. No. 16/645,315, 39 pages.
Lulu Miao, et al., "PD-L1 and c-MET Expression and Survival in Patients with Small Cell Lung Cancer" Oncotarget, vol. 8, No. 33, 2017, pp. 53978-53988.
Patrick A. Ott, et al. "Pembrolizumab in Patients With Extensive-Stage Small-Cell Lung Cancer: Results From the Phase Ib KEYNOTE-028 Study" Journal of Clinical Oncology, vol. 35, No. 34, Dec. 1, 2017, pp. 3823-3829 and cover pages.
Steppeler F. et al., "Chiral Thioureas-Preparation and Significance in Asymmetric Synthesis and Medicinal Chemistry", Molecules, Jan. 18, 2020, vol. 25, No. 2, Article No. 401, pp. 1 to 56, https://doi.org/10.3390/molecules25020401.
Yamashita, Kazuko et al., "Development. of an On-line Sample Enrichment System Coupled to ESI-TOFMS—Challenge to highly sensitive structural elucidation of impurities of agrochemicals and pharmaceuticals-", Sumitomo Chemical, 2002, vol. II, pp. 56-64 (with English Abstract).
Murakami, Tomonori et al., "Structure Elucidation of Impurities in Pharmaceuticals by HPLC Hyphenated Techniques", Chromatography, 2012, vol. 33, No. 3, pp. 179-190 (with English Abstract).

(56) References Cited

OTHER PUBLICATIONS

International Search Report issued in PCT/JP2021/005272 mailed Mar. 30, 2021 (with English Translation).
Written Opinion of International Search Report issued in PCT /JP2021/005272 mailed Mar. 30, 2021 (with English Translation).
Shang, et al, "Cabozantinib-based combination therapy for the treatment of hepatocellular carcinoma", Gut 2021;70:1746-1757. doi:10.1136/gutjnl-2020-320716.
Shang, et al, "Cabozantinib based combination therapy for the treatment of Hepatocellular Carcinoma"—Supplemental Material; *Gut* 2020;0:1-12. doi: 10.1136/gutjnl-2020-320716.
Reference ID: 4375294. Highlights of Prescribing Information These highlights do not include all the information needed to use Cabometyx safely and effectively. See full prescribing information for Cabometyx.
Loeuillard, "Targeting tumor-associated macrophages and granulocytic myeloid-derived suppressor cells augments PD-1 blockade in cholangiocarcinoma", *J Clin Invest*. 2020;130(10):5380-5396.
Supplementary Methods—YAP Signature Differential Expression Analysis.
Fujita, et al, High Potency VEGFRs/MET/FMS Triple Blockade by TAS-115 Concomitantly Suppresses Tumor Progression and Bone Destruction in Tumor-Induced Bone Disease Model with Lung Carcinoma Cells, PLOS ONE | DOI:10.1371/journal.pone.0164830 Oct. 13, 2016.
Yamada—"Therapeutic potential of TAS-115 via c-MET and PDGFRα signal inhibition for synovial sarcoma", BMC Cancer (2017) 17:334 DOI 10.1186/s12885-017-3324-3.
Fujita, et al., High Potency VEGFRs/MET/FMS Triple Blockade by TAS-115Concomitantly Suppresses Tumor Progression and BoneDestruction in Tumor-Induced Bone Disease Model withLung Carcinoma Cells, Published: Oct. 13, 2016, 13 pages.
Pin Wu, et al., PD-L1 and Survival in Solid Tumors: A Meta-Analysis; PLOS ONE | DOI:10.1371/journal.pone.0131403 Jun. 26, 2015, 15 Pages.
Ze-Jun Zhou, et al, PD-L1 over-expression and survival in patients with non-small cell lung cancer: a meta-analysis, *Transl Lung Cancer Res* 2015;4(2):203-208, 6 pages.
Yaqi Li, et al, Prognostic impact of programed cell death-1 (PD-1) and PD-ligand 1 (PD-L1) expression in cancer cells and tumor infiltrating lymphocytes in colorectal cancer, Molecular Cancer, (2016) 15:55, 15 pages.
Jian Guan, MD, PhD, et al., Programmed Death Ligand-1 (PD-L1) Expression in the Programmed Death Receptor-1 (PD-1)/PD-L1 Blockade, Review Article, Arch Pathol Lab Med—vol. 141, Jun. 2017, 11 pages.
Noah Frydenlund BS, MS, et al., PD-L1 and immune escape: insights from melanoma and other lineage-unrelated malignancies, Elsevier, Human Pathology, Jun. 2017; 21 pages.
Ke Ma. et al. ,PD-L1 and PD-1 expression correlate with prognosis in extrahepatic cholangiocarcinoma, Oncology Letters 14: 250-256, 2017, 7 pages.
Lulu Miao, et al., PD-L1 and c-MET expression and survival in patients with small cell lung cancer; Oncotarget, 2017, vol. 8, (No. 33), pp. 53978-53988, 11 pages.
Runze Shang, et al, Cabozantinib based combination therapy for the treatment of Hepatocellular Carcinoma, *Gut* 2020;0:1-12. doi: 10.1136, 52 pages.
Runze Shang, et al., Cabozantinib-based combination therapy for the treatment of hepatocellular carcinoma, Hepatology, Gut 2021;70:1746-1757. doi:10.1136/gutjnl-2020-320716, 12 pages.
Dong Wang, et al. "Immune Checkpoint Inhibitor Associated Myocarditis and Cardiomyopathy: A Translational Review" Biology 2023, 12, 472, 17 pages.
European Office Action issued in EP Application 18 854 415.9, on Sep. 18, 2024.
European Office Action issued in EP Application 18 854 415.9, on Nov. 12, 2023.
Response to Communication dated Dec. 12, 2023, filed on Jun. 7, 2024 in EP Application 18 854 415.9.
Response to Communication dated May 19, 2021, filed on Oct. 11, 2021 in EP Application 18 854 415.9.

* cited by examiner

ANTITUMOR AGENT AND ANTITUMOR EFFECT POTENTIATOR

This application claims benefit of JP application 2017-173352 filed Sep. 8, 2017 and PCT/JP2018/033108 filed Sep. 6, 2018. The contents of both priority applications are incorporated herein by reference.

TECHNICAL FIELD

The present invention relates to an antitumor agent, an antitumor effect potentiator, and a kit preparation combining an acyl thiourea compound or a salt thereof with an immune checkpoint molecule regulator.

BACKGROUND ART

4-[2-Fluoro-4-[[[(2-phenylacetyl)amino]thioxomethyl]amino]-phenoxy]-7-methoxy-N-methyl-6-quinolinecarboxamide is an antitumor agent having reduced side effects (PTL 1), and has been known to show desirable antitumor-effect potentiating effect when used with other antitumor agents (PTL 2). A recent study reports that such an acyl thiourea compound inhibits osteoclast differentiation by way of CSF1R inhibition, and shows antitumor effects in an osteolytic bone metastasis tumor model (NPL 1). Inhibitory effect against enzymes of the TAM family has also been shown (NPL 2).

In addition to being involved in osteoclast differentiation, CSF1R is also a factor that modulates proliferation of macrophages occurring as precursor cells of osteoclasts, and proliferation of tumor-associated macrophages involved in tumor malignancy, and the effects of its inhibitor on immunity have been reported (NPL 3, 4). Protein tyrosine kinase 3 (TYRO3), AXL (AXL receptor tyrosine kinase), and MERTK (MER proto-oncogene, tyrosine kinase) of the TAM Family are also known to have important roles in intratumoral microenvironment factors such as tumor-associated macrophages, bone marrow-derived immunosuppressor cells, intratumoral vascular endothelial cells, and tumor-associated fibroblasts (NPL 5, 6).

Cancer immunotherapy has been developed as a new form of cancer therapy. Activation of adaptive immune reaction is initiated by binding of an antigenic peptide-MHC complex and T-cell receptor (TCR). The binding is regulated by costimulation or coinhibition due to binding of the B7 family—a costimulatory molecule—and its receptor CD28 family. Specifically, T cells require two characteristic signaling events for antigen-specific activation, and T cells stimulated solely by antigen without costimulation with the B7 family assume a state of unresponsiveness (anergy), inducing immune tolerance.

By taking advantage of this mechanism, cancer cells escape from immunological surveillance and continue their growth by inhibiting activation of antigen-specific T cells. For cancer treatment, it is therefore considered effective to enhance costimulation or block coinhibition to induce an anti-tumor immune response in the body of a cancer patient and thereby control a tumor escaping from immunity. To this end, various types of immunotherapies that target costimulatory molecules (stimulatory costimulatory molecules) or coinhibitory molecules (suppressive costimulatory molecules) have been proposed (NPL 7). For example, nivolumab (human IgG4 monoclonal antibody against human PD-1) has been used for the treatment of cancers such as malignant melanoma as an immune checkpoint molecule regulator that activates T cells by inhibiting binding of PD-1 and its ligands (PD-L1 and PD-L2) (NPL 1, NPL 8). Involvement of a tumor-associated macrophage as a resistance mechanism against such cancer immunotherapy has also been indicated (NPL 9, 10).

An acyl thiourea compound represented by the general formula (I) below or a salt thereof is known as a c-Met inhibitor (PTL 1, 3), and there are reports combining the c-Met inhibitor with other antitumor agents (PTL 2).

CITATION LIST

Patent Literature

PTL 1: WO2009/125597
PTL 2: WO2013/100014
PTL 3: WO2016/175305

Non Patent Literature

NPL 1: PLoS ONE, 11(10): e0164830 (2016)
NPL 2: Molecular Cancer Therapeutics, 12 (12): 2685-2696 (2013)
NPL 3: Cancer Cell, 25: 846-859 (2014)
NPL 4: Frontiers in Immunology, 5: Article 489 (2014)
NPL 5: Cancers, 8(10), 97: 8100097 (2016)
NPL 6: Cancers, 8(11), 103: 8110103 (2016)
NPL 7: Nat. Rev. Cancer, 12 (4): 252-264 (2012)
NPL 8: The New England Journal of Medicine, 366; 26: 2443-2454 (2012)
NPL 9: Cell, 168(4): 707-723 (2017)
NPL 10: Science Translational Medicine, 9 (389): eaal 3604 (2017)

SUMMARY OF INVENTION

Technical Problem

Concerning NPL 8 to NPL 10, combined use of an anticancer agent and an anti-macrophage agent is expected to produce an enhanced effect.

Concerning PTL 2, combined use of the acyl thiourea compound or salts thereof with an immune checkpoint molecule regulator is not known.

It is accordingly an object of the present invention to provide a novel antitumor agent and a novel antitumor effect potentiator that show marked antitumor effects with reduced side effects.

Solution to Problem

The present inventor studied the antitumor effects produced by a combination of an acyl thiourea compound represented by general formula (I) or a salt thereof and an immune checkpoint molecule regulator, and found that these medicinal agents produce prominently higher antitumor effects with no serious side effects when used in combination than when used alone by themselves. It was also found that the acyl thiourea compound or salts thereof greatly reduce the tumor-associated macrophages, which play a major role in the suppression of anti-tumor immune response.

The present inventor also found that an acyl thiourea compound represented by general formula (I) or salts thereof have an immunostimulatory effect.

Specifically, the present invention provides the following inventions [1] to [21].

[1] An antitumor agent characterized by coadministration of an acyl thiourea compound represented by the following general formula (I) or a salt thereof, and an immune checkpoint molecule regulator.

[Chem. 1]

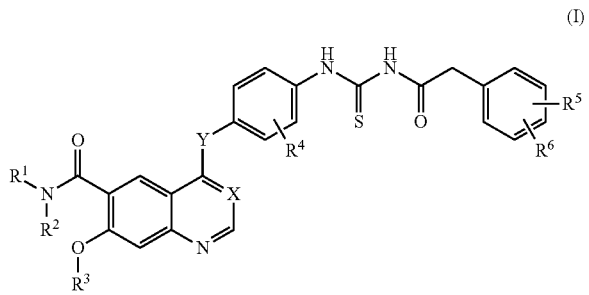

(I)

(In general formula (I),
X represents CH or N;
Y represents O or NH;
$R^1$, $R^2$, and $R^3$ each independently represent a hydrogen atom, a $C_{1-10}$ alkyl group that may have a substituent, a $C_{3-10}$ cyclic alkyl group that may have a substituent, a $C_{6-14}$ aromatic hydrocarbon group that may have a substituent, or a saturated or unsaturated heterocyclic group that may have a substituent, or $R^1$ and $R^2$ may be bound to each other with the nitrogen atom to form a nitrogen-containing heterocyclic ring that may have a substituent; and
$R^4$, $R^5$, and $R^6$ each independently represent a hydrogen atom, a halogen atom, a $C_{1-6}$ alkyl group, a $C_{1-6}$ alkoxy group, a $C_{1-6}$ alkylamino group, an aromatic hydrocarbon group that may have a substituent, or a saturated or unsaturated heterocyclic group that may have a substituent, or $R^5$ and $R^6$ may be bound to each other with the phenyl ring to form a ring.)

[2] The antitumor agent according to [1], wherein the acyl thiourea compound is a compound represented by the general formula (I), in which X represents CH, Y represents O, $R^1$ represents a hydrogen atom or a $C_{1-6}$ alkyl group, $R^2$ represents a hydrogen atom, a $C_{1-10}$ alkyl group that may have a substituent, or a saturated or unsaturated heterocyclic group that may have a substituent, or $R^1$ and $R^2$ may be bound to each other with the nitrogen atom to form a nitrogen-containing heterocyclic ring that may have a substituent, $R^3$ represents a $C_{1-6}$ alkyl group that may have a substituent, $R^4$ represents a halogen atom, and $R^5$ and $R^6$ each independently represent a hydrogen atom or a halogen atom.

[3] The antitumor agent according to [1] or [2], wherein the acyl thiourea compound is a compound represented by the general formula (I), in which X represents CH, Y represents O, $R^1$ represents a hydrogen atom or a methyl group, $R^2$ represents a hydrogen atom, a $C_{1-10}$ alkyl group that may have a substituent, or a 5- to 7-membered heterocyclic group that may have a substituent and having one to two nitrogen or oxygen atoms, $R^3$ represents a methyl or propyl group that may have a 5- to 7-membered heterocyclic group having one to two nitrogen or oxygen atoms, $R^4$ represents a fluorine atom, $R^5$ represents a hydrogen atom, and $R^6$ represents a halogen atom.

More specifically, the antitumor agent according to [1] is an antitumor agent in which the acyl thiourea compound is a compound selected from the following group of compounds:

4-(2-Fluoro-4-(3-(2-phenylacetyl)thioureido)phenoxy)-N-(3-isopropoxypropyl)-7-methoxyquinoline-6-carboxamide N-((2,2-Dimethyl-1,3-dioxolan-4-yl)methyl)-4-(2-fluoro-4-(3-(2-phenylacetypthioureido)phenoxy)-7-methoxyquinoline-6-carboxamide N-(2,3-Dihydroxypropyl)-4-(2-fluoro-4-(3-(2-phenylacetyl)thioureido)phenoxy)-7-methoxyquinoline-6-carboxamide 4-(2-Fluoro-4-(3-(2-phenylacetyl)thioureido)phenoxy)-7-methoxy-N-(pyridin-3-ylmethyl)quinoline-6-carboxamide 4-(2-Fluoro-4-(3-(2-phenylacetyl)thioureido)phenoxy)-7-methoxy-N-(3-(2-oxopyrrolidin-1-yl)propyl)quinoline-6-carboxamide 4-(2-Fluoro-4-(3-(2-phenylacetyl)thioureido)phenoxy)-7-methoxy-N-methylquinoline-6-carboxamide 4-(2-Fluoro-4-(3-(2-phenylacetyl)thioureido)phenoxy)-7-methoxy-N-(methoxyethyl)quinoline-6-carboxamide N-(2-(Diethylamino)ethyl)-4-(2-fluoro-4-(3-(2-phenylacetyl)thioureido)phenoxy)-7-methoxyquinoline-6-carboxamide 4-(2-Fluoro-4-(3-(2-phenylacetyl)thioureido)phenoxy)-7-methoxy-N-(2-morphohnoethyl)quinoline-6-carboxamide 4-(2-Fluoro-4-(3-(2-phenylacetyl)thioureido)phenoxy)-N-(2-(2-hydroxyethoxy)ethyl)-7-methoxyquinoline-6-carboxamide N-(2-Acetamidoethyl)-4-(2-fluoro-4-(3-(2-phenylacetyl)thioureido)phenoxy)-7-methoxyquinoline-6-carboxamide N-(1,3-Dihydroxypropan-2-yl)-4-(2-fluoro-4-(3-(2-phenylacetyl)thioureido)phenoxy)-7-methoxyquinoline-6-carboxamide tert-Butyl-4-(4-(2-fluoro-4-(3-(2-phenylacetyl)thioureido)phenoxy)-7-methoxyquinoline-6-carboxamide)-6-carboxamide)piperidine-1-carboxylate 4-(2-Fluoro-4-(3-(2-phenylacetyl)thioureido)phenoxy)-7-methoxy-N-(piperidin-4-yl)quinoline-6-carboxamide N-(1-(Ethylcarbamoyl)piperidin-4-yl)-4-(2-fluoro-4-(3-(2-phenylacetyl)thioureido)phenoxy)-7-methoxyquinoline-6-carboxamide 4-(2-Fluoro-4-(3-(2-phenylacetyl)thioureido)phenoxy)-7-methoxy-N-(2-oxoazepan-3-yl)quinoline-6-carboxamide 4-(2-Fluoro-4-(3-(2-phenylacetyl)thioureido)phenoxy)-7-methoxy-N-(2-oxo-2-(pyrrolidin-1-yl)ethyl)quinoline-6-carboxamide N-(1-Acetylpiperidin-4-yl)-4-(2-fluoro-4-(3-(2-phenylacetyl)thioureido)phenoxy)-7-methoxyquinoline-6-carboxamide 4-(2-Fluoro-4-(3-(2-(4-fluorophenypacetyl)thiourcido)phenoxy)-7-methoxy-N-(2-oxoazepan-3-yl)quinoline-6-carboxamide (S)-4-(2-Fluoro-4-(3-(2-phenylacetyl)thioureido)phenoxy)-N-(2-(3-fluoropyrrolidin-1-yl)-2-oxoethyl)-7-methoxyquinoline-6-carboxamide 4-(2-Fluoro-4-(3-(2-phenylacetyl)thioureido)phenoxy)-7-methoxy-N-(2-morpholino-2-oxoethyl)quinoline-6-carboxamide N-(2-(Dimethylamino)-2-oxoethyl)-4-(2-fluoro-4-(3-(2-phenylacetyl)thioureido)phenoxy)-7-methoxyquinoline-6-carboxamide 4-(2-Fluoro-4-(3-(2-(4-fluorophenyl)acetyl)thioureido)phenoxy)-N-(2-hydroxybutyl)-7-methoxyquinoline-6-carboxamide 4-(2-Fluoro-4-(3-(2-phenylacetyl)thioureido)phenoxy)-N-(2-hydroxy-2-methylpropyl)-7-methoxyquinoline-6-carboxamide 4-(2-Fluoro-4-(3-(2-phenylacetyl)thioureido)phenoxy)-N-((1-hydroxycyclohexyl)methyl)-7-methoxyquinoline-6-carboxamide 4-(2-Fluoro-4-(3-(2-phenylacetyl)thioureido)phenoxy)-N-((4-hydroxytetrahydro-2H-pyran-4-yl)methyl)-7-methoxyquinoline-6-carboxamide 4-(2-Fluoro-4-(3-(2-phenylacetyl)thioureido)phenoxy)-7-methoxy-N-(2-(methylsulfonyl)ethyl)quinoline-6-carboxamide

[4] The antitumor agent according to any one of [1] to [3], wherein the immune checkpoint molecule regulator is at least one selected from a PD-1 pathway antagonist, an ICOS pathway agonist, a CTLA-4 pathway antagonist, and a CD28 pathway agonist.

[5] The antitumor agent according to any one of [1] to [4], wherein the immune checkpoint molecule regulator is at least one selected from a PD-1 pathway antagonist, a CTLA-4 pathway antagonist, and a CD28 pathway agonist.

[6] The antitumor agent according to any one of [1] to [5], wherein the immune checkpoint molecule regulator is at least one of a PD-1 pathway antagonist and a CTLA-4 pathway antagonist.

[7] The antitumor agent according to any one of [1] to [6], wherein the immune checkpoint molecule regulator is a PD-1 pathway antagonist.

[8] The antitumor agent according to any one of [4] to [7], wherein the PD-1 pathway antagonist is at least one selected from an anti-PD-1 antibody, an anti-PD-L1 antibody, and an anti-PD-L2 antibody.

[9] The antitumor agent according to [8], wherein the anti-PD-1 antibody is at least one of nivolumab and pembrolizumab, and the anti-PD-L1 antibody is at least one selected from atezolizumab, durvalumab, and avelumab.

[10] The antitumor agent according to any one of [4] to [6], wherein the CTLA-4 pathway antagonist is an anti-CTLA-4 antibody.

[11] The antitumor agent according to [10], wherein the anti-CTLA-4 antibody is at least one of ipilimumab and tremelimumab.

[12] The antitumor agent according to any one of [1] to [3], wherein the acyl thiourea compound represented by the general formula (I) or a salt thereof is 4-(2-fluoro-4-(3-(2-phenylacetyl)thioureido)phenoxy)-7-methoxy-N-methylquinoline-6-carboxamide or a salt thereof.

[13] The antitumor agent according to any one of [1] to [12], wherein a target cancer is at least one selected from melanoma, kidney cancer, lung cancer, head and neck cancer, Hodgkin's lymphoma, bladder cancer, colon cancer, liver cancer, stomach cancer, osteosarcoma and soft tissue sarcoma, breast cancer, and prostate cancer.

[14] An antitumor effect potentiator for immune checkpoint molecule regulators comprising: an acyl thiourea compound represented by the following general formula (I) or a salt thereof as an active component.

[Chem. 2]

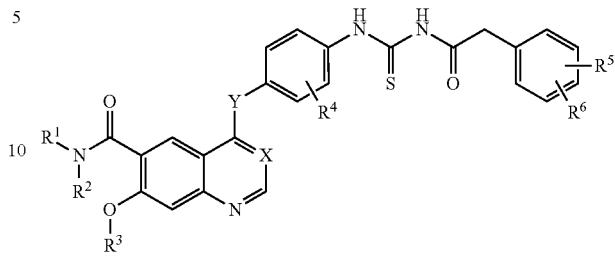

(I)

(In general formula (I),
X represents CH or N;
Y represents O or NH;
$R^1$, $R^2$, and $R^3$ each independently represent a hydrogen atom, a $C_{1-10}$ alkyl group that may have a substituent, a $C_{3-10}$ cyclic alkyl group that may have a substituent, a $C_{6-14}$ aromatic hydrocarbon group that may have a substituent, or a saturated or unsaturated heterocyclic group that may have a substituent, or $R^1$ and $R^2$ may be bound to each other with the nitrogen atom to form a nitrogen-containing heterocyclic ring that may have a substituent; and
$R^4$, $R^5$, and $R^6$ each independently represent a hydrogen atom, a halogen atom, a $C_{1-6}$ alkyl group, a $C_{1-6}$ alkoxy group, a $C_{1-6}$ alkylamino group, an aromatic hydrocarbon group that may have a substituent, or a saturated or unsaturated heterocyclic group that may have a substituent, or $R^5$ and $R^6$ may be bound to each other with the phenyl ring to form a ring.)

[15] An antitumor agent for treating a cancer patient to whom an immune checkpoint molecule regulator is administered, comprising:
an acyl thiourea compound or a salt thereof,
wherein the acyl thiourea compound is a compound represented by the following general formula (I).

[Chem. 3]

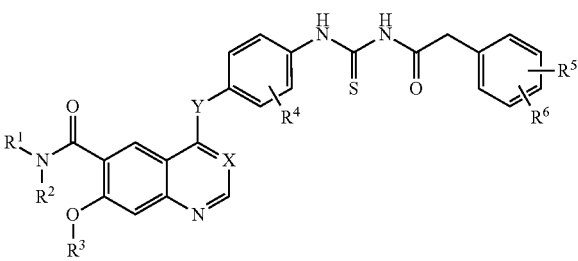

(I)

(In general formula (I),
X represents CH or N;
Y represents O or NH;
$R^1$, $R^2$, and $R^3$ each independently represent a hydrogen atom, a $C_{1-10}$ alkyl group that may have a substituent, a $C_{3-10}$ cyclic alkyl group that may have a substituent, a $C_{6-14}$ aromatic hydrocarbon group that may have a substituent, or a saturated or unsaturated heterocyclic group that may have a substituent, or $R^1$ and $R^2$ may be bound to each other with the nitrogen atom to form a nitrogen-containing heterocyclic ring that may have a substituent; and R[4], R[5], and R[6] each independently represent a hydrogen atom, a halogen atom, a $C_{1-6}$ alkyl group, a $C_{1-6}$ alkoxy group, a $C_{1-6}$ alkylamino group, an aromatic hydrocarbon group that may have a substituent, or a saturated or unsaturated heterocyclic group that may have a substituent, or R[5] and R[6] may be bound to each other with the phenyl ring to form a ring.)

[16] An antitumor agent for treating a cancer patient to whom an acyl thiourea compound or a salt thereof is administered, comprising:

an immune checkpoint molecule regulator, wherein the acyl thiourea compound is a compound represented by the following general formula (I).

[Chem. 4]

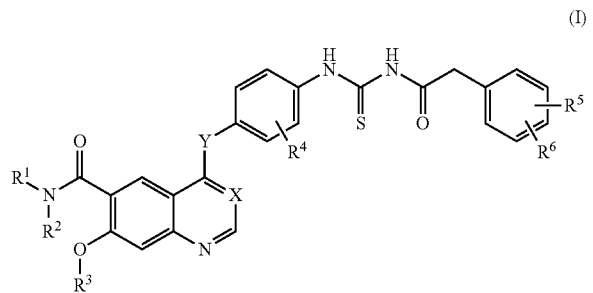
(I)

(In general formula (I),

X represents CH or N;

Y represents O or NH;

R[1], R[2], and R[3] each independently represent a hydrogen atom, a $C_{1-10}$ alkyl group that may have a substituent, a $C_{3-10}$ cyclic alkyl group that may have a substituent, a $C_{6-14}$ aromatic hydrocarbon group that may have a substituent, or a saturated or unsaturated heterocyclic group that may have a substituent, or R[1] and R[2] may be bound to each other with the nitrogen atom to form a nitrogen-containing heterocyclic ring that may have a substituent; and R[4], R[5], and R[6] each independently represent a hydrogen atom, a halogen atom, a $C_{1-10}$ alkyl group, a $C_{1-6}$ alkoxy group, a $C_{1-6}$ alkylamino group, an aromatic hydrocarbon group that may have a substituent, or a saturated or unsaturated heterocyclic group that may have a substituent, or R[5] and R[6] may be bound to each other with the phenyl ring to form a ring.)

[17] An antitumor agent, comprising:

an acyl thiourea compound or a salt thereof in combination with an immune checkpoint molecule regulator, wherein the acyl thiourea compound is a compound represented by the following general formula (I).

[Chem. 5]

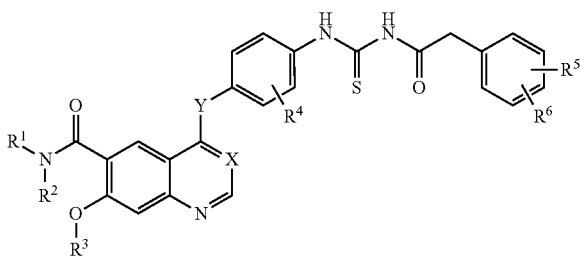
(I)

(In general formula (I),

X represents CH or N;

Y represents O or NH;

R[1], R[2], and R[3] each independently represent a hydrogen atom, a $C_{1-10}$ alkyl group that may have a substituent, a $C_{3-10}$ cyclic alkyl group that may have a substituent, a $C_{6-14}$ aromatic hydrocarbon group that may have a substituent, or a saturated or unsaturated heterocyclic group that may have a substituent, or R[1] and R[2] may be bound to each other with the nitrogen atom to form a nitrogen-containing heterocyclic ring that may have a substituent; and R[4], R[5], and R[6] each independently represent a hydrogen atom, a halogen atom, a $C_{1-6}$ alkyl group, a $C_{1-6}$ alkoxy group, a $C_{1-6}$ alkylamino group, an aromatic hydrocarbon group that may have a substituent, or a saturated or unsaturated heterocyclic group that may have a substituent, or R[5] and R[6] may be bound to each other with the phenyl ring to form a ring.)

[18] An immunostimulant, comprising:

an acyl thiourea compound of the following general formula (I) or a salt thereof as an active component.

[Chem. 6]

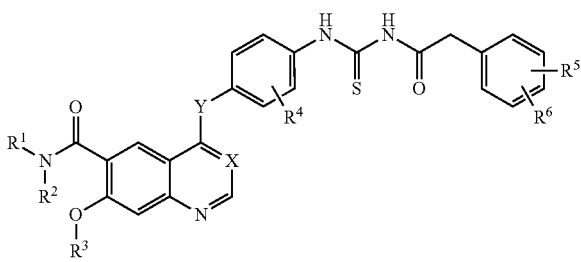
(I)

(In general formula (I),

X represents CH or N;

Y represents O or NH;

R[1], R[2], and R[3] each independently represent a hydrogen atom, a $C_{1-10}$ alkyl group that may have a substituent, a $C_{3-10}$ cyclic alkyl group that may have a substituent, a $C_{6-14}$ aromatic hydrocarbon group that may have a substituent, or a saturated or unsaturated heterocyclic group that may have a substituent, or R[1] and R[2] may be bound to each other with the nitrogen atom to form a nitrogen-containing heterocyclic ring that may have a substituent; and R[4], R[5], and R[6] each independently represent a hydrogen atom, a halogen atom, a $C_{1-6}$ alkyl group, a $C_{1-6}$ alkoxy group, a $C_{1-6}$ alkylamino group, an aromatic hydrocarbon group that may have a substituent, or a saturated or unsaturated heterocyclic group that may have a substituent, or $R^5$ and $R^6$ may be bound to each other with the phenyl ring to form a ring.)

[19] A pharmaceutical composition for potentiating effects of a medicament that acts on immunity to prevent or treat disease,
the pharmaceutical composition comprising:
an acyl thiourea compound represented by the following general formula (I) or a salt thereof.

[Chem. 7]

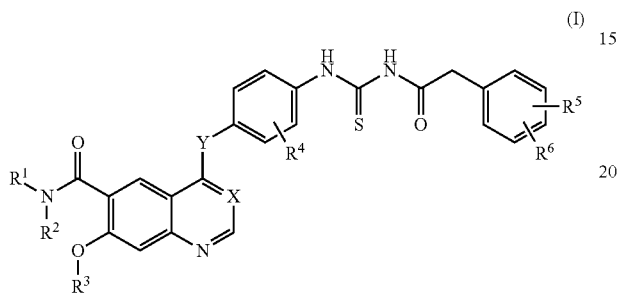

(I)

(In general formula (I),
X represents CH or N;
Y represents O or NH;
$R^1$, $R^2$, and $R^3$ each independently represent a hydrogen atom, a $C_{1-10}$ alkyl group that may have a substituent, a $C_{3-10}$ cyclic alkyl group that may have a substituent, a $C_{6-14}$ aromatic hydrocarbon group that may have a substituent, or a saturated or unsaturated heterocyclic group that may have a substituent, or $R^1$ and $R^2$ may be bound to each other with the nitrogen atom to form a nitrogen-containing heterocyclic ring that may have a substituent; and
$R^4$, $R^5$, and $R^6$ each independently represent a hydrogen atom, a halogen atom, a $C_{1-6}$ alkyl group, a $C_{1-6}$ alkoxy group, a $C_{1-6}$ alkylamino group, an aromatic hydrocarbon group that may have a substituent, or a saturated or unsaturated heterocyclic group that may have a substituent, or $R^5$ and $R^6$ may be bound to each other with the phenyl ring to form a ring.)

[20] A pharmaceutical composition, comprising:
an acyl thiourea compound or a salt thereof with a medicament that acts on immunity to prevent or treat disease in combination,
wherein the acyl thiourea compound is a compound represented by the following general formula (I).

[Chem. 8]

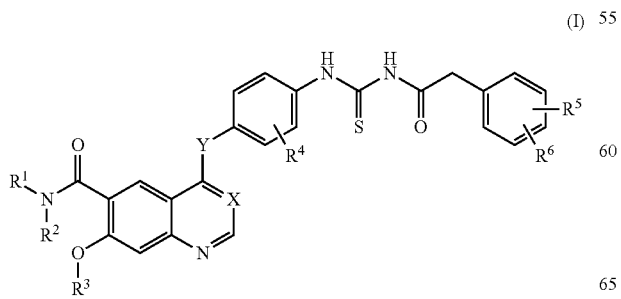

(I)

(In general formula (I),
X represents CH or N;
Y represents O or NH;
$R^1$, $R^2$, and $R^3$ each independently represent a hydrogen atom, a $C_{1-10}$ alkyl group that may have a substituent, a $C_{3-10}$ cyclic alkyl group that may have a substituent, a $C_{6-14}$ aromatic hydrocarbon group that may have a substituent, or a saturated or unsaturated heterocyclic group that may have a substituent, or $R^1$ and $R^2$ may be bound to each other with the nitrogen atom to form a nitrogen-containing heterocyclic ring that may have a substituent; and
$R^4$, $R^5$, and $R^6$ each independently represent a hydrogen atom, a halogen atom, a $C_{1-6}$ alkyl group, a $C_{1-6}$ alkoxy group, a $C_{1-6}$ alkylamino group, an aromatic hydrocarbon group that may have a substituent, or a saturated or unsaturated heterocyclic group that may have a substituent, or $R^5$ and $R^6$ may be bound to each other with the phenyl ring to form a ring.)

[21] An immunostimulant for treating a patient to whom a medicament that acts on immunity to prevent or treat disease is administered, comprising:
an acyl thiourea compound or a salt thereof,
wherein the acyl thiourea compound is a compound represented by the following general formula (I).

[Chem. 9]

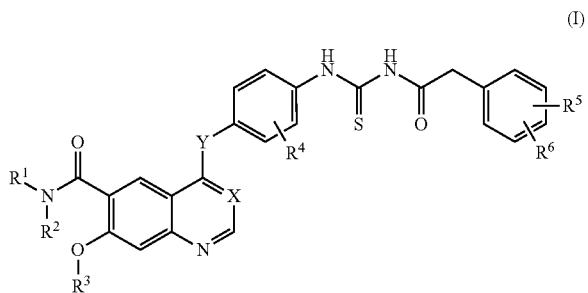

(I)

(In general formula (I),
X represents CH or N;
Y represents O or NH;
$R^1$, $R^2$, and $R^3$ each independently represent a hydrogen atom, a $C_{1-10}$ alkyl group that may have a substituent, a $C_{3-10}$ cyclic alkyl group that may have a substituent, a $C_{6-14}$ aromatic hydrocarbon group that may have a substituent, or a saturated or unsaturated heterocyclic group that may have a substituent, or $R^1$ and $R^2$ may be bound to each other with the nitrogen atom to form a nitrogen-containing heterocyclic ring that may have a substituent; and
$R^4$, $R^5$, and $R^6$ each independently represent a hydrogen atom, a halogen atom, a $C_{1-6}$ alkyl group, a $C_{1-6}$ alkoxy group, a $C_{1-6}$ alkylamino group, an aromatic hydrocarbon group that may have a substituent, or a saturated or unsaturated heterocyclic group that may have a substituent, or $R^5$ and $R^6$ may be bound to each other with the phenyl ring to form a ring.)

The present invention also relates to the following embodiments.
(1) A pharmaceutical composition for prevention and/or treatment of a tumor, comprising an acyl thiourea compound represented by the foregoing general formula (I) or a salt thereof, and an immune checkpoint molecule regulator.

(2) An antitumor agent for use in prevention and/or treatment of a tumor by coadministration of an acyl thiourea compound represented by the foregoing general formula (I) or a salt thereof, and an immune checkpoint molecule regulator.

(3) An antitumor agent for use in prevention and/or treatment or a tumor, comprising an acyl thiourea compound represented by the foregoing general formula (I) or a salt thereof in combination with an immune checkpoint molecule regulator.

(4) An antitumor agent for use in treatment of a cancer patient to whom an immune checkpoint molecule regulator is administered, the antitumor agent comprising an acyl thiourea compound represented by the foregoing general formula (I) or a salt thereof.

(5) Use of an acyl thiourea compound represented by the foregoing general formula (I) or a salt thereof and an immune checkpoint molecule regulator for manufacture of an antitumor agent.

(6) Use of an acyl thiourea compound represented by the foregoing general formula (I) or a salt thereof for manufacture of an antitumor agent to be used for a cancer patient to whom an immune checkpoint molecule regulator is administered.

(7) An acyl thiourea compound represented by the foregoing general formula (I) or a salt thereof for potentiating antitumor effects of an immune checkpoint molecule regulator.

(8) Use of an acyl thiourea compound represented by the foregoing general formula (I) or a salt thereof for potentiating antitumor effects of an immune checkpoint molecule regulator.

(9) Use of an acyl thiourea compound represented by the foregoing general formula (I) or a salt thereof for manufacture of an antitumor effect potentiator for an immune checkpoint molecule regulator.

(10) A method for preventing and/or treating a tumor, comprising the step of administering a therapeutically and/or prophylactically effective amount of a combination of an acyl thiourea compound represented by the foregoing general formula (I) or a salt thereof and an immune checkpoint molecule regulator to a patient.

(11) A method for preventing and/or treating a tumor, comprising the step of administering a therapeutically and/or prophylactically effective amount of an acyl thiourea compound represented by the foregoing general formula (I) or a salt thereof to a cancer patient to whom an immune checkpoint molecule regulator is administered.

(12) A method for preventing and/or treating a tumor, comprising the step of administering a therapeutically and/or prophylactically effective amount of an immune checkpoint molecule regulator to a cancer patient to whom an acyl thiourea compound represented by the foregoing general formula (I) or a salt thereof is administered.

(13) An immune checkpoint molecule regulator for use in treatment and/or prevention of a tumor in a cancer patient to whom an acyl thiourea compound represented by the foregoing general formula (I) or a salt thereof is administered.

(14) Use of an immune checkpoint molecule regulator for manufacture of an antitumor agent to be used for treatment and/or prevention of a tumor in a cancer patient to whom an acyl thiourea compound represented by the foregoing general formula (I) or a salt thereof is administered.

(15) A method for potentiating antitumor effects, comprising the step of administering a therapeutically and/or prophylactically effective amount of an acyl thiourea compound represented by the foregoing general formula (I) or a salt thereof to a cancer patient to whom an immune checkpoint molecule regulator is administered.

(16) A product comprising an acyl thiourea compound represented by the foregoing general formula (I) or a salt thereof and an immune checkpoint molecule regulator as a combined preparation (hereinafter, referred to also as "kit preparation") to be used simultaneously, successively or with intervals for prevention and/or treatment of a tumor.

Advantageous Effects of Invention

An antitumor agent of the present invention enables a cancer treatment that is highly antitumor effect (particularly, tumor reduction effect, and delaying of tumor growth (life-prolonging effect)) while reducing side effects, increasing the chances of long-term survival of cancer patients. An immunostimulant of the present invention provides a novel treatment for various diseases (for example, various infections, immunodeficiency diseases, and tumors) that are ameliorable by immunostimulation.

DESCRIPTION OF EMBODIMENTS

Figure 1:
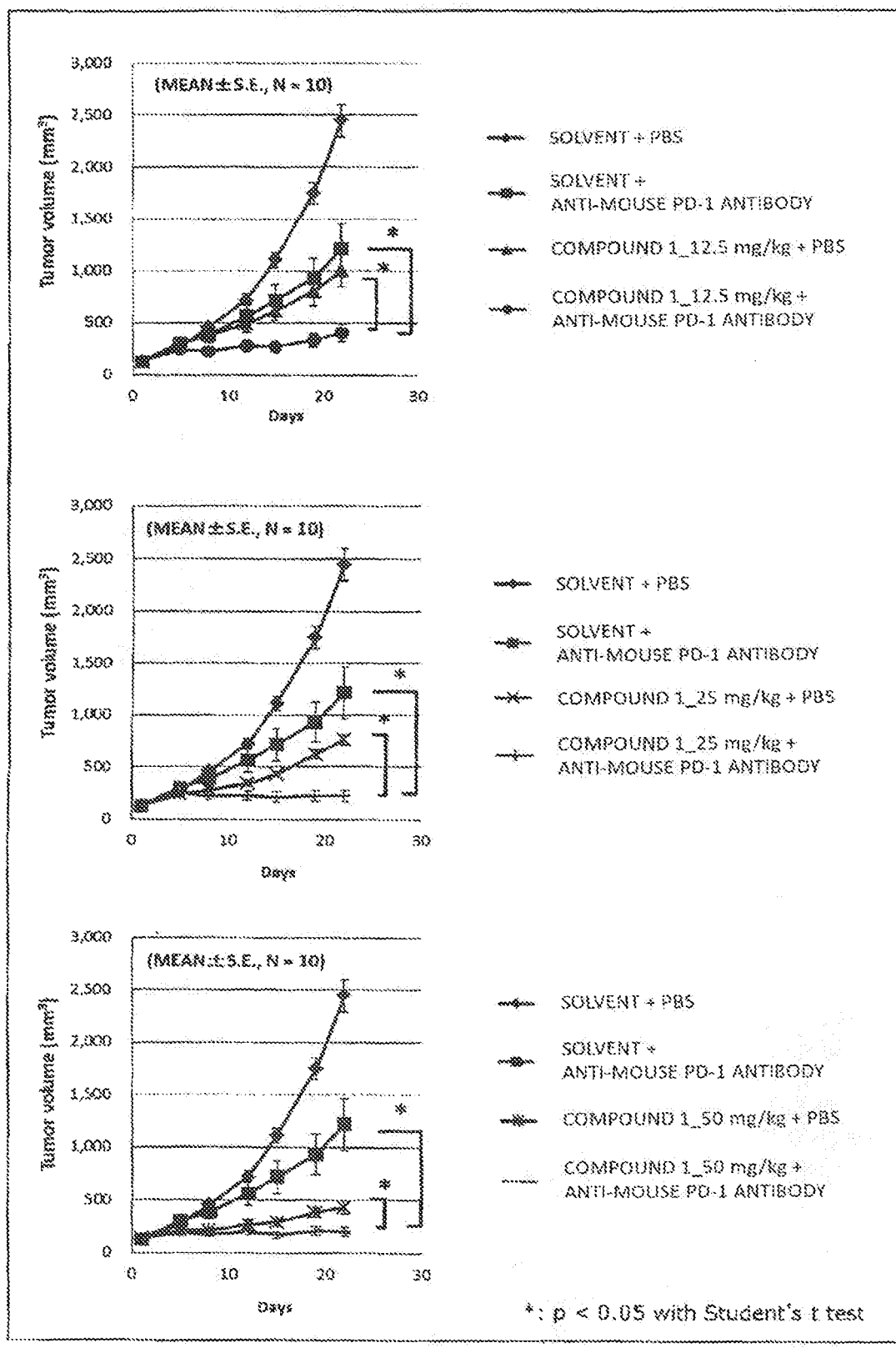
FIG. 1 represents graphs showing the effects of combinations of compound 1 and anti-mouse PD-1 antibody in a mouse model transplanted with mouse colon cancer cell line MC38.

The present invention relates to an antitumor agent, an antitumor effect potentiator, and a kit preparation characterized by coadministration of an acyl thiourea compound represented by general formula (I) or a salt thereof, and an immune checkpoint molecule regulator (particularly, anti-PD-1 antibody), and to use of these agents, a method for treating tumors, a method for preventing tumors, and a method for potentiating antitumor effects. The present invention also relates to an immunostimulant. As used herein, the language "to be coadministered" is synonymous with "to be used so as to be coadministered".

Acyl Thiourea Compound

In the present invention, acyl thiourea compounds or salts thereof are compounds represent by the following general formula (I) or salts thereof.

[Chem. 10]

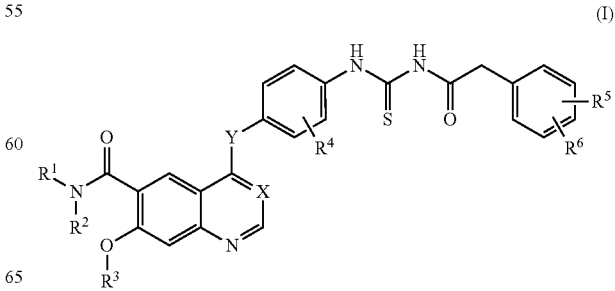

(I)

(In general formula (I),
X represents CH or N;
Y represents O or NH;
$R^1$, $R^2$, and $R^3$ each independently represent a hydrogen atom, a $C_{1-10}$ alkyl group that may have a substituent, a $C_{3-10}$ cyclic alkyl group that may have a substituent, a $C_{6-14}$ aromatic hydrocarbon group that may have a substituent, or a saturated or unsaturated heterocyclic group that may have a substituent, or $R^1$ and $R^2$ may be bound to each other with the nitrogen atom to form a nitrogen-containing heterocyclic ring that may have a substituent; and
$R^4$, $R^5$, and $R^6$ each independently represent a hydrogen atom, a halogen atom, a $C_{1-6}$ alkyl group, a $C_{1-6}$ alkoxy group, a $C_{1-6}$ alkylamino group, an aromatic hydrocarbon group that may have a substituent, or a saturated or unsaturated heterocyclic group that may have a substituent, or $R^5$ and $R^6$ may be bound to each other with the phenyl ring to form a ring.)

As used herein, the language "may have a substituent" used in conjunction with a given structure means that the structure may have one, two, or more "substituents" at its chemically acceptable positions. As used herein, the language "having a substituent" used in conjunction with a given structure means that the structure has one, two, or more "substituents" at its chemically acceptable positions.

The type, number, and position of a substituent on the structure are not particularly limited, and may be the same or different when two or more substituents exist. Examples of the "substituent" include a halogen atom, a hydroxyl group, a cyano group, a nitro group, an alkyl group of 1 to 6 carbon atoms, a cycloalkyl group of 3 to 7 carbon atoms, an alkenyl group of 2 to 6 carbon atoms, an alkoxy group of 1 to 6 carbon atoms, a carbonyl group, an aminocarbonyl group, a sulfonyl group, an alkylsulfonyl group, an amino group, a mono or dialkylamino group, a carbonylamino group, an acyl group, an oxo group, a saturated or unsaturated heterocyclic group, and an aromatic hydrocarbon group of 6 to 14 carbon atoms. When these substituents are present, the number of substituents is typically one to three.

The numbers shown in lower case following the symbol C represent the number of carbon atoms. For example, "$C_{1-6}$" means one to six carbon atoms.

In general formula (I), X is CH or N, preferably CH.
In general formula (I), Y is O or NH, preferably O.
In general formula (I), "$C_{1-10}$ alkyl group" in the "$C_{1-10}$ alkyl group that may have a substituent" represented by $R^1$, $R^2$, and $R^3$ represents a linear or branched alkyl group of 1 to 10 carbon atoms, for example, such as a methyl group, an ethyl group, an n-propyl group, an isopropyl group, an n-butyl group, a sec-butyl group, a tert-butyl group, an n-pentyl group, an n-hexyl group, an n-octynyl group, or an n-decanyl group.

In general formula (I), "substituent" in the "$C_{1-10}$ alkyl group that may have a substituent" represented by $R^1$, $R^2$, and $R^3$ may be, for example, any of the substituents exemplified above.

In general formula (I), "$C_{3-10}$ cyclic alkyl group" in the "$C_{3-10}$ cyclic alkyl group that may have a substituent" represented by $R^1$, $R^2$, and $R^3$ represents a cyclic alkyl group of 3 to 10 carbon atoms, for example, such as a cyclopropyl group, a cyclobutyl group, a cyclopentyl group, or a cyclohexyl group.

In general formula (I), "substituent" in the "$C_{3-10}$ alkyl group that may have a substituent" represented by $R^1$, $R^2$, and $R^3$ may be, for example, any of the substituents exemplified above.

In general formula (I), "$C_{6-14}$ aromatic hydrocarbon group" in the "$C_{6-14}$ aromatic hydrocarbon group that may have a substituent" represented by $R^1$, $R^2$, and $R^3$ represents a monocyclic or bicyclic aromatic hydrocarbon group of 6 to 14 carbon atoms, for example, such as a phenyl group or a naphthyl group.

In general formula (I), "substituent" in the "$C_{6-14}$ aromatic hydrocarbon group that may have a substituent" represented by $R^1$, $R^2$, and $R^3$ may be, for example, any of the substituents exemplified above.

In general formula (I), "saturated or unsaturated heterocyclic group" in the "saturated or unsaturated heterocyclic group that may have a substituent" represented by $R^1$, $R^2$, and $R^3$ represents a monocyclic or bicyclic saturated or unsaturated heterocyclic group having one or two oxygen atoms, one or two nitrogen atoms, or one or two sulfur atoms, for example, such as a pyrrolidinyl group, a piperidinyl group, a piperazinyl group, a hexamethyleneimino group, a morpholino group, a thiomorpholino group, a homopiperidinyl group, an imidazolyl group, a thienyl group, a furyl group, a pyrrolyl group, an oxazolyl group, an isoxazolyl group, a thiazolyl group, an isothiazolyl group, a pyrazolinyl group, a triazolyl group, a tetrazolyl group, a pyridyl group, a pyrazil group, a pyrimidinyl group, an pyridazyl group, an indolyl group, an isoindolyl group, an indazolyl group, a methylenedioxyphenyl group, an ethylenedioxyphenyl group, a benzofuranyl group, a dihydrobenzofuranyl group, a benzoimidazolyl group, a benzooxazole group, a benzothiazolyl group, a purinyl group, a quinolyl group, an isoquinolyl group, a quinazolinyl group, or a quinoxalyl group. Preferably, "saturated or unsaturated heterocyclic group" in the "saturated or unsaturated heterocyclic group that may have a substituent" represented by $R^1$, $R^2$, and $R^3$ is a 5- to 7-membered saturated heterocyclic ring having one or two nitrogen atoms or one or two oxygen atoms, more preferably a 5- to 7-membered saturated heterocyclic ring having one or two nitrogen atoms, for example, such as a pyrrolidinyl group, a piperidinyl group, a piperazinyl group, or a hexamethyleneimino group.

In general formula (I), "substituent" in the "saturated or unsaturated heterocyclic group that may have a substituent" represented by $R^1$, $R^2$, and $R^3$ may be, for example, any of the substituents exemplified above, and is preferably a $C_{1-6}$ alkylcarbonyl group, a $C_{1-6}$ alkylaminocarbonyl group, a $C_{1-6}$ alkoxycarbonyl group, or an oxo group, more preferably a tert-butoxycarbonyl group, an ethylaminocarbonyl group, an acetyl group, or an oxo group.

In general formula (I), "nitrogen-containing heterocyclic ring" in the "nitrogen-containing heterocyclic ring that may have a substituent" formed by binding of $R^1$ and $R^2$ with the nitrogen atom may be, for example, a pyrrolidinyl group, a piperidinyl group, a piperazinyl group, or a morpholino group.

In general formula (I), "substituent" in the "nitrogen-containing heterocyclic ring that may have a substituent" formed by binding of $R^1$ and $R^2$ with the nitrogen atom may be, for example, any of the substituents exemplified above.

In general formula (I), the "halogen atom" represented by $R^4$, $R^5$, and $R^6$ may be, for example, a fluorine atom, a bromine atom, a chlorine atom, or an iodine atom, and is preferably a fluorine atom.

In general formula (I), the "$C_{1-6}$ alkyl group" represented by $R^4$, $R^5$, and $R^6$ represents a linear or branched alkyl group of 1 to 6 carbon atoms, for example, such as a methyl group, an ethyl group, an n-propyl group, an isopropyl group, an n-butyl group, a sec-butyl group, a tert-butyl group, an n-pentyl group, or an n-hexyl group.

In general formula (I), the "$C_{1-6}$ alkoxy group" represented by $R^4$, $R^5$, and $R^6$ represents a linear or branched alkoxy group of 1 to 6 carbon atoms, for example, such as a methoxy group, an ethoxy group, an n-propyloxy group, an isopropyloxy group, an n-butyloxy group, a sec-butyloxy group, a tert-butyloxy group, an n-pentyloxy group, or an n-hexyloxy group.

In general formula (I), the "$C_{1-6}$ alkylamino group" represented by $R^4$, $R^5$, and $R^6$ represents an amino group monosubstituted or disubstituted with the $C_{1-6}$ alkyl group above. Examples include a methylamino group, an ethylamino group, a dimethylamino group, a methylethylamino group, an n-propylamino group, an isopropylamino group, an n-butylamino group, a sec-butylamino group, a tert-butylamino group, an n-pentylamino group, and an n-hexylamino group.

In general formula (I), "aromatic hydrocarbon group" in the "aromatic hydrocarbon group that may have a substituent" represented by $R^4$, $R^5$, and $R^6$ represents an aromatic hydrocarbon group of 6 to 14 carbon atoms, as with the case of the "$C_{6-14}$ aromatic hydrocarbon group". Preferred examples include a phenyl group and a naphthyl group.

In general formula (I), "substituent" in the "aromatic hydrocarbon group that may have a substituent" represented by $R^4$, $R^5$, and $R^6$ may be, for example, any of the substituents exemplified above.

In general formula (I), "saturated or unsaturated heterocyclic ring" in the "saturated or unsaturated heterocyclic ring that may have a substituent" represented by $R^4$, $R^5$, and $R^6$ represents a monocyclic or bicyclic saturated or unsaturated heterocyclic group having one or two oxygen atoms, one or two nitrogen atoms, or one or two sulfur atoms, as with the foregoing case. Examples include a pyrrolidinyl group, a piperidinyl group, a piperazinyl group, a morpholino group, a thiomorpholino group, a homopiperidinyl group, an imidazolyl group, a thienyl group, a furyl group, a pyrrolyl group, an oxazolyl group, an isoxazolyl group, a thiazolyl group, an isothiazolyl group, a pyrazolinyl group, a triazolyl group, a tetrazolyl group, a pyridyl group, a pyrazil group, a pyrimidinyl group, a pyridazyl group, an indolyl group, an isoindolyl group, an indazolyl group, a methylenedioxyphenyl group, an ethylenedioxyphenyl group, a benzofuranyl group, a dihydrobenzofuranyl group, a benzoimidazolyl group, a benzothiazolyl group, a purinyl group, a quinolyl group, an isoquinolyl group, a quinazolinyl group, and a quinoxalyl group. Preferably, "saturated or unsaturated heterocyclic ring" in the "saturated or unsaturated heterocyclic ring that may have a substituent" represented by $R^4$, $R^5$, and $R^6$ is a 5- to 7-membered saturated heterocyclic ring having one or two nitrogen atoms, for example, such as a pyrrolidinyl group, a piperidinyl group, or a piperazinyl group.

In general formula (I), "substituent" in the "saturated or unsaturated heterocyclic ring that may have a substituent" represented by $R^4$, $R^5$, and $R^6$ may be, for example, any of the substituents exemplified above.

Examples of the "ring" formed by binding of $R^5$ and $R^6$ with the phenyl ring include a naphthalene ring, a quinoline ring, a quinazoline ring, an indole ring, a benzimidazole ring, a methylenedioxyphenyl ring, and an ethylenedioxyphenyl ring.

The following more specifically describes the substituents in the general formula (I) above.

Examples of the halogen atom include a fluorine atom, a bromine atom, a chlorine atom, and an iodine atom.

Examples of the alkyl group of 1 to 6 carbon atoms include a methyl group, an ethyl group, an isopropyl group, an n-butyl group, a sec-butyl group, a tert-butyl group, an n-pentyl group, and an n-hexyl group.

Examples of the cycloalkyl group of 3 to 7 carbon atoms include a cyclopropyl group, a cyclobutyl group, a cyclopentyl group, and a cyclohexyl group.

Examples of the alkenyl group of 2 to 6 carbon atoms include a vinyl group and a 2-propenyl group.

Examples of the alkoxy group of 1 to 6 carbon atoms include a methoxy group, an ethoxy group, an isopropyloxy group, and an n-butyloxy group.

The saturated or unsaturated heterocyclic group represents a monocyclic or bicyclic saturated or unsaturated heterocyclic group having one or two oxygen atoms, one or two nitrogen atoms, or one or two sulfur atoms, such as above. Examples include a pyrrolidinyl group, a piperidinyl group, a piperazinyl group, a morpholino group, a thiomorpholino group, a homopiperidinyl group, an imidazolyl group, a thienyl group, a furyl group, a pyrrolyl group, an oxazolyl group, an isoxazolyl group, a thiazolyl group, an isothiazolyl group, a pyrazolinyl group, a triazolyl group, a tetrazolyl group, a pyridyl group, a pyrazil group, a pyrimidinyl group, a pyridazyl group, an indolyl group, an isoindolyl group, an indazolyl group, a methylenedioxyphenyl group, an ethylenedioxyphenyl group, a benzofuranyl group, a dihydrobenzofuranyl group, a benzoimidazolyl group, a benzooxazole group, a benzothiazolyl group, a purinyl group, a quinolyl group, an isoquinolyl group, a quinazolinyl group, and a quinoxalyl group.

Examples of the aromatic hydrocarbon group of 6 to 14 carbon atoms include a phenyl group and a naphthyl group.

Preferred examples of $R^1$ include a hydrogen atom and a $C_{1-10}$ alkyl group. $R^1$ is more preferably a hydrogen atom or a $C_{1-6}$ alkyl group, particularly preferably a hydrogen atom or a methyl group.

Preferably, $R^2$ is a hydrogen atom, a $C_{1-10}$ alkyl group that may have a substituent, or a saturated or unsaturated heterocyclic group that may have a substituent.

Preferred examples of the substituent on the $C_{1-10}$ alkyl group include groups selected from a halogen atom, a hydroxyl group, a $C_{1-6}$ alkoxy group, an amino group, a $C_{1-6}$ alkylamino group, a di($C_{1-6}$ alkylamino group, a hydroxy $C_{1-6}$ alkoxy group, a $C_{1-6}$ alkanoylamino group, an aminocarbonyl group, a $C_{1-6}$ alkylaminocarbonyl group, a di($C_{1-6}$ alkyl)aminocarbonyl group, a $C_{3-10}$ cycloalkyl group, a $C_{1-6}$ alkylsulfonyl group, the heterocyclic group mentioned above, the heterocyclic carbonyl group mentioned above, and an oxo group. Preferably, the heterocyclic ring is a 5- to 7-membered heterocyclic ring having one to two nitrogen atoms or one to two oxygen atoms, for example, such as pyrrolidinyl, piperidinyl, piperazinyl, pyridyl, homopiperidinyl, morpholinyl, dioxolan, and dioxane.

The heterocyclic ring may be substituted with, for example, a halogen atom, a hydroxyl group, an oxo group, a $C_{1-6}$ alkoxy group, a $C_{1-6}$ alkyl group, a $C_{1-6}$ alkanoyl group, a $C_{1-6}$ alkylaminocarbonyl group, a $C_{1-6}$ alkoxycarbonyl group, an amino group, a $C_{1-6}$ alkylamino group, or a di($C_{1-6}$ alkyl)amino group.

The saturated or unsaturated heterocyclic group that may have a substituent represented by $R^2$ is preferably a 5- to 7-membered heterocyclic group having one to two nitrogen atoms or one to two oxygen atoms, for example, such as a pyrrolidinyl group, a piperidinyl group, a piperazinyl group, a pyridyl group, a homopiperidinyl group, a morpholinyl group, a dioxolan group, and an oxane group.

The heterocyclic group may be substituted with, for example, a halogen atom, a hydroxyl group, an oxo group, a $C_{1-6}$ alkoxy group, a $C_{1-6}$ alkyl group, a $C_{1-6}$ alkanoyl group, a $C_{1-6}$ alkylaminocarbonyl group, or a $C_{1-6}$ alkoxycarbonyl group.

Preferably, $R^1$ and $R^2$, with the nitrogen atom bound thereto, form a nitrogen-containing heterocyclic ring that may have a substituent.

Preferably, $R^3$ is a $C_{1-10}$ alkyl group that may have a substituent, more preferably a $C_{1-6}$ alkyl group that may have a substituent, particularly preferably a methyl group that may have a substituent, or a propyl group that may have a substituent. The substituent is preferably a 5- to 7-membered heterocyclic group having one to two nitrogen atoms or one to two oxygen atoms, more preferably a morpholino group.

$R^4$ is preferably a halogen atom, particularly preferably a fluorine atom. Preferably, $R^4$ is substituted at position 2.

$R^5$ and $R^6$ are preferably hydrogen atoms or halogen atoms. Particularly preferably, one of $R^5$ and $R^6$ is a hydrogen atom, and the other is a halogen atom. Preferably, $R^5$ and $R^6$ are substituted at positions 3 and 4. When $R^5$ is a hydrogen atom and $R^6$ is a halogen atom, $R^6$ is substituted at preferably position 4.

Among the compounds represented by general formula (I), the following compounds are preferred in the present invention.

4-(2-Fluoro-4-(3-(2-phenylacetyl)thioureido)phenoxy)-N-(3-isopropoxypropyl)-7-methoxyquinoline-6-carboxamide N-((2,2-Dimethyl-1,3-dioxolan-4-yl)methyl)-4-(2-fluoro-4-(3-(2-phenylacetyl)thioureido)phenoxy)-7-methoxyquinoline-6-carboxamide N-(2,3-Dihydroxypropyl)-4-(2-fluoro-4-(3-(2-phenylacetyl)thioureido)phenoxy)-7-methoxyquinoline-6-carboxamide 4-(2-Fluoro-4-(3-(2-phenylacetyl)thioureido)phenoxy)-7-methoxy-N-(pyridin-3-ylmethyl)quinoline-6-carboxamide 4-(2-Fluoro-4-(3-(2-phenylacetyl)thioureido)phenoxy)-7-methoxy-N-(3-(2-oxopyrrolidin-1-yl)propyl)quinoline-6-carboxamide 4-(2-Fluoro-4-(3-(2-phenylacetyl)thioureido)phenoxy)-7-methoxy-N-methylquinoline-6-carboxamide 4-(2-Fluoro-4-(3-(2-phenylacetyl)thioureido)phenoxy)-7-methoxy-N-(methoxyethyl)quinoline-6-carboxamide N-(2-(Diethylamino)ethyl)-4-(2-fluoro-4-(3-(2-phenylacetyl)thioureido)phenoxy)-7-methoxyquinoline-6-carboxamide 4-(2-Fluoro-4-(3-(2-phenylacetyl)thioureido)phenoxy)-7-methoxy-N-(2-morpholinoethyl)quinoline-6-carboxamide 4-(2-Fluoro-4-(3-(2-phenylacetyl)thioureido)phenoxy)-N-(2-(2-hydroxyethoxy)ethyl)-7-methoxyquinoline-6-carboxamide N-(2-Acetamidoethyl)-4-(2-fluoro-4-(3-(2-phenylacetyl)thiourcido)phenoxy)-7-methoxyquinoline-6-carboxamide N-(1,3-Dihydroxypropan-2-yl)-4-(2-fluoro-4-(3-(2-phenylacetyl)thioureido)phenoxy)-7-methoxyquinoline-6-carboxamide tert-Butyl-4-(4-(2-fluoro-4-(3-(2-phenylacetyl)thioureido)phenoxy)-7-methoxyquinoline-6-carboxamide)-6-carboxamide)piperidine-1-carboxylate 4-(2-Fluoro-4-(3-(2-phenylacetyl)thioureido)phenoxy)-7-methoxy-N-(piperidin-4-yl)quinoline-6-carboxamide N-(1-(Ethylcarbamoyl)piperidin-4-yl)-4-(2-fluoro-4-(3-(2-phenylacetyl)thioureido)phenoxy)-7-methoxyquinoline-6-carboxamide 4-(2-Fluoro-4-(3-(2-phenylacetyl)thioureido)phenoxy)-7-methoxy-N-(2-oxoazepan-3-yl)quinoline-6-carboxamide 4-(2-Fluoro-4-(3-(2-phenylacetyl)thioureido)phenoxy)-7-methoxy-N-(2-oxo-2-(pyrrolidin-1-yl)ethyl)quinoline-6-carboxamide N-(1-Acetylpiperidin-4-yl)-4-(2-fluoro-4-(3-(2-phenylacetyl)thioureido)phenoxy)-7-methoxyquinoline-6-carboxamide 4-(2-Fluoro-4-(3-(2-(4-fluorophenypacetyl)thioureido)phenoxy)-7-methoxy-N-(2-oxoazepan-3-yl)quinoline-6-carboxamide (S)-4-(2-Fluoro-4-(3-(2-phenylacetyl)thioureido)phenoxy)-N-(2-(3-fluoropyrrolidin-1-yl)-2-oxoethyl)-7-methoxyquinoline-6-carboxamide 4-(2-Fluoro-4-(3-(2-phenylacetyl)thioureido)phenoxy)-7-methoxy-N-(2-morpholino-2-oxoethyl)quinoline-6-carboxamide N-(2-(Dimethylamino)-2-oxoethyl)-4-(2-fluoro-4-(3-(2-phenylacetyl)thioureido)phenoxy)-7-methoxyquinoline-6-carboxamide 4-(2-Fluoro-4-(3-(2-(4-fluorophenyl)acetyl)thioureido)phenoxy)-N-(2-hydroxybutyl)-7-methoxyquinoline-6-carboxamide 4-(2-Fluoro-4-(3-(2-phenylacetyl)thioureido)phenoxy)-N-(2-hydroxy-2-methylpropyl)-7-methoxyquinoline-6-carboxamide 4-(2-Fluoro-4-(3-(2-phenylacetyl)thioureido)phenoxy)-N-((1-hydroxycyclohexyl)methyl)-7-methoxyquinoline-6-carboxamide 4-(2-Fluoro-4-(3-(2-phenylacetyl)thioureido)phenoxy)-N-((4-hydroxytetrahydro-2H-pyran-4-yl)methyl)-7-methoxyquinoline-6-carboxamide 4-(2-Fluoro-4-(3-(2-phenylacetyl)thioureido)phenoxy)-7-methoxy-N-(2-(methylsulfonyl)ethyl)quinoline-6-carboxamide.

Among the compounds represented by general formula (I), particularly preferred in the present invention is 4-(2-fluoro-4-(3-(2-phenylacetyl)thioureido)phenoxy)-7-methoxy-N-methylquinoline-6-carboxamide.

The acyl thiourea compound represented by general formula (I) of the present invention includes a solvate such as a stereoisomer, an optical isomer, or a hydrate.

The acyl thiourea compound represented by general formula (I) of the present invention may be a salt, and the salt is preferably a pharmacologically acceptable salt. Examples of such salts include salts of inorganic bases, salts of organic bases, salts with inorganic acid, salts with organic acid, salts with acidic amino acid, and salts with basic amino acid.

Specifically, examples of the salts of inorganic bases include alkali metal salts such as sodium salts and potassium salts, and alkali-earth metal salts such as magnesium salts and calcium salts.

Examples of the salts of organic bases include trimethylamine, triethylamine, pyridine, N-methylpyridine, N-methylpyrrolidone, ethanolamine, diethanolamine, triethanolamine, and dicyclohexylamine.

Examples of the inorganic acids include hydrochloric acid, sulfuric acid, hydrobromic acid, hydroiodic acid, nitric acid, and phosphoric acid.

Examples of the organic acids include formic acid, acetic acid, propionic acid, malonic acid, succinic acid, glutaric acid, fumaric acid, maleic acid, lactic acid, malic acid, citric acid, tartaric acid, benzenesulfonic acid, p-toluenesulfonic acid, and methanesulfonic acid (methylsulfonic acid).

Examples of the acidic amino acids include glutamic acid and aspartic acid. Examples of the basic amino acids include lysine, asparagine, and ornithine.

The acyl thiourea compound represented by general formula (I) of the present invention may have a form of a pharmacologically acceptable prodrug. The pharmacologically acceptable prodrug may be any compound, provided that it transforms into an acyl thiourea compound represented by general formula (I) under the physiological conditions of the body, for example, such as by hydrolysis, oxidation, or reduction with gastric acid or enzyme. Examples of such compounds include ester compounds for modifying carboxyl group, such as methyl ester, ethyl ester, propyl ester, phenyl ester, carboxyoxymethyl ester, and ethoxycarbonyl ester. Typical examples of compounds that form such prodrugs include compounds that transform into acyl thiourea compounds represented by general formula (I) under the physiological conditions described in *Drug Development*, Vol. 7, pp. 163 to 198 (1990), Hirokawa Publishing Company.

A specific example of the acyl thiourea compound is 4-(2-fluoro-4-(3-(2-phenylacetyl)thioureido)phenoxy)-7-methoxy-N-methylquinoline-6-carboxamide (will be referred to as "compound 1") of the following structure.

[Chem. 11]

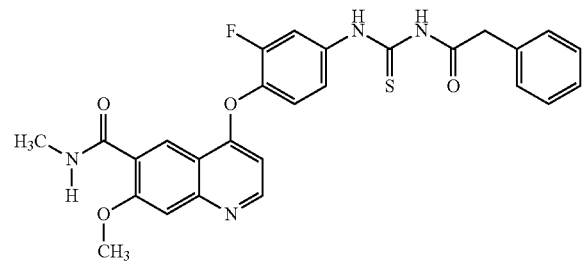

Compound 1 can be synthesized using a known method. For example, synthesis of compound 1 may be based on WO2009/125597 (PTL 1) or WO2016/175305 (PTL 3).

The acyl thiourea compound represented by general formula (I) or salts thereof of the present invention directly acts on an immune checkpoint molecule by itself to induce an anti-tumor immune response in the body of a cancer patient and thereby control a tumor escaping from immunity.

Immune Checkpoint Molecule Regulator

An immune checkpoint molecule regulator of the present invention directly acts on an immune checkpoint molecule to induce an anti-tumor immune response in the body of a cancer patient and thereby control a tumor escaping from immunity.

The immune checkpoint molecule regulator may be, for example, a substance that facilitates the function of a costimulatory molecule (stimulatory costimulatory molecule), or a substance that suppresses the function of a coinhibitory molecule (suppressive costimulatory molecule).

Examples of the immune checkpoint molecule include molecules of the B7 family (e.g., B7-1, B7-2, PD-L1, PD-L2), the CD28 family (e.g., CTLA-4, PD-1), the TNF superfamily (4-1BBL, OX40L), and the TNF receptor superfamily (4-1BB, OX40). The immune checkpoint molecule regulator may be a substance that targets such an immune checkpoint molecule. For example, the immune checkpoint molecule regulator may be a PD-1 pathway antagonist, an ICOS pathway agonist, a CTLA-4 pathway antagonist, a CD28 pathway agonist, a BTLA pathway antagonist, or a 4-1BB pathway agonist.

The immune checkpoint molecule regulator of the present invention is preferably at least one selected from a PD-1 pathway antagonist, an ICOS pathway agonist, a CTLA-4 pathway antagonist, and a CD28 pathway agonist. From the standpoint of reducing side effects, the immune checkpoint molecule regulator of the present invention is more preferably at least one selected from a PD-1 pathway antagonist, a CTLA-4 pathway antagonist, and a CD28 pathway agonist, even more preferably at least one of a PD-1 pathway antagonist and a CTLA-4 pathway antagonist, further preferably a PD-1 pathway antagonist, or a PD-1 pathway antagonist and a CTLA-4 pathway antagonist.

The PD-1 pathway antagonist inhibits the immunosuppressive signal from PD-1 expressed on T cells, or from its ligand PD-L1 or PD-L2. Examples of the PD-1 pathway antagonist include an anti-PD-1 antibody, an anti-PD-L1 antibody, an anti-PD-L2 antibody, a PD-1 extracellular domain, a PD-L1 extracellular domain, a PD-L2 extracellular domain, PD-1-Ig (a fusion protein of PD-1 extracellular domain and the FC region of Ig), PD-L1-Ig, PD-L2-Ig, PD-1 siRNA, PD-L1 siRNA, and PD-L2 siRNA. The PD-1 pathway antagonist is preferably at least one selected from an anti-PD-1 antibody, an anti-PD-L1 antibody, and an anti-PD-L2 antibody, more preferably at least one of an anti-PD-1 antibody and an anti-PD-L1 antibody, particularly preferably an anti-PD-1 antibody.

The CTLA-4 pathway antagonist inhibits the immunosuppressive signal from CTLA-4 expressed on T cells, or from its ligand B7-1(CD80) or B7-2 (CD86). The CTLA-4 pathway antagonist is preferably an anti-CTLA-4 antibody, a CTLA-4 extracellular domain, CTLA-4-Ig, an anti-B7-1 (CD80) antibody, or an anti-B7-2 (CD86) antibody, more preferably an anti-CTLA-4 antibody or CTLA-4-Ig, particularly preferably an anti-CTLA-4 antibody.

Examples of these antibodies include immunoglobulins (e.g., IgA, IgD, IgE, IgG, IgM, IgY), Fab fragments, F(ab')$_2$ fragments, single-chain antibody fragments (scFv), single-domain antibodies, and diabodies (Nat. Rev. Immunol., 6:343-357, 2006). The antibodies may be monoclonal antibodies or polyclonal antibodies, including, for example, human antibodies, humanized antibodies, chimeric antibodies, mouse antibodies, llama antibodies, and chicken antibodies.

Preferably, the antibodies are humanized IgG monoclonal antibodies or human IgG monoclonal antibodies.

Examples of the anti-PD-1 antibody in the present invention include nivolumab, pembrolizumab, cemiplimab, and spartalizumab. Preferred are nivolumab and pembrolizumab.

Examples of the anti-PD-L1 antibody in the present invention include atezolizumab, durvalumab, and avelumab. Preferred is atezolizumab.

Examples of the anti-CTLA-4 antibody in the present invention include ipilimumab and tremelimumab. Preferred is ipilimumab.

Examples of the CTLA-4-Ig in the present invention include abatacept. Preferred is abatacept.

These antibodies can be produced by using a common known antibody producing method.

The anti-PD-1 antibody is commercially available or scheduled to be available as nivolumab or pembrolizumab. The anti-PD-L1 antibody is commercially available or scheduled to be available as atezolizumab, durvalumab, or avelumab. The anti-CTLA-4 antibody is commercially available or scheduled to be available as ipilimumab or tremelimumab. The CTLA-4-Ig is commercially available or scheduled to be available as abatacept. It is also possible to use these commercially available products.

In the present invention, when using two or more immune checkpoint molecule regulators, for example, the anti-PD-1 antibody and the anti-CTLA-4 antibody may be used in combination, or a bispecific antibody capable of binding to both PD-1 and CTLA-4 may be used. Examples of the bispecific antibody include XmAb20717 (PD-1×CTLA-4).

The acyl thiourea compounds represented by general formula (I) or salts thereof have an immunostimulatory effect against humans and other mammals, including, for example, monkeys, mice, rats, rabbits, dogs, cats, cows, horses, pigs, and sheep. As used herein, "immunostimulatory effect" means the effect to activate immune cells, and induce cell division or production of various cytokines. The acyl thiourea compounds represented by general formula (I) or salts thereof have the effect to stimulate immune cells, particularly T cells. The present invention relates to an immunostimulant containing an acyl thiourea compound represented by general formula (I) or a salt thereof, and to a method for stimulating immunity in a patient in need of prevention or treatment, wherein the method includes administering an effective amount of an acyl thiourea compound represented by general formula (I) or a salt thereof as an immunostimulant to the patient.

With the immunostimulatory effect of acyl thiourea compounds represented by general formula (I) or salts thereof, the acyl thiourea compound represented by general formula (I) or a salt thereof is able to prevent or treat diseases that can be ameliorated by way of immunostimulation, for example, such as various infections, immunodeficiency diseases, diseases caused by weakened immune function due to aging, and virus-related tumors.

Examples of infections that can be prevented or treated with the acyl thiourea compound represented by general formula (I) or a salt thereof include parasitic infections (for example, Trypanosoma, malaria parasites, Toxoplasma), bacterial infections (for example, pneumococcus, *Mycobacterium tuberculosis, Staphylococcus aureus, Bacillus anthracis, Vibrio cholerae, mycoplasma, Helicobacter pylori*), and viral infections (for example, human T-cell leukemia virus (HTLV-1), human immunodeficiency virus (HIV), papillomavirus (HPV), Epstein-Barr virus (EBV), cytomegalovirus (CMV), influenza virus (FLU), hepatitis B virus (HBV), herpes virus, hepatitis C virus (HCV), SARS coronavirus, MERS coronavirus, dengue virus, and Ebola virus).

In another aspect, the present invention relates to a pharmaceutical composition containing an acyl thiourea compound represented by general formula (I) or a salt thereof for the immunostimulatory prevention or treatment of infection, and an acyl thiourea compound represented by general formula (I) or a salt thereof for the immunostimulatory prevention or treatment of infection, and to a method for immunostimulatory prevention or treatment of an infection in a patient in need of prevention or treatment, wherein the method includes administering an effective amount of an acyl thiourea compound represented by general formula (I) or a salt thereof to the patient.

Examples of immunodeficiency diseases that can be prevented or treated with an acyl thiourea compound represented by general formula (I) or a salt thereof include congenital immunodeficiency diseases and acquired immune diseases, particularly, acquired immunodeficiency caused by human immunodeficiency virus (HIV) infection. In this respect, another aspect of the present invention relates to a pharmaceutical composition containing an acyl thiourea compound represented by general formula (I) or a salt thereof for the immunostimulatory treatment of immunodeficiency disease, and an acyl thiourea compound represented by general formula (I) or a salt thereof for the immunostimulatory treatment of immunodeficiency disease, and to a method for immunostimulatory prevention or treatment of an immunodeficiency disease in a patient in need of treatment, wherein the method includes administering an effective amount of an acyl thiourea compound represented by general formula (I) or a salt thereof to the patient.

Specific examples of diseases caused by weakened immune function due to aging and that can be prevented or treated with an acyl thiourea compound represented by general formula (I) or salts thereof include pneumonia. In this respect, another aspect of the present invention relates to a pharmaceutical composition containing an acyl thiourea compound represented by general formula (I) or a salt thereof for the immunostimulatory prevention or treatment of a disease caused by weakened immune function due to aging, and an acyl thiourea compound represented by general formula (I) or a salt thereof for the immunostimulatory prevention or treatment of a disease caused by weakened immune function due to aging, and to a method for immunostimulatory prevention or treatment of a disease caused by weakened immune function due to aging in a patient in need of prevention or treatment, wherein the method includes administering an effective amount of an acyl thiourea compound represented by general formula (I) or a salt thereof to the patient.

Specific examples of virus-related tumors, or tumors caused by viral infection, that can be prevented or treated with an acyl thiourea compound represented by general formula (I) or salts thereof include Burkitt lymphoma, hepatocellular carcinoma, cervical cancer, adult T-cell leukemia, Kaposi's sarcoma, and head and neck cancer. In this respect, another aspect of the present invention relates to a pharmaceutical composition containing an acyl thiourea compound represented by general formula (I) or a salt thereof for the immunostimulatory prevention or treatment of virus-related tumor, and an acyl thiourea compound represented by general formula (I) or a salt thereof for the immunostimulatory prevention or treatment of virus-related tumor, and to a method for immunostimulatory prevention or treatment of a virus-related tumor in a patient in need of prevention or treatment, wherein the method includes administering an effective amount of an acyl thiourea compound represented by general formula (I) or a salt thereof to the patient.

Acyl thiourea compounds represented by general formula (I) or salts thereof have an immunostimulatory effect that can potentiate effects of a medicament that acts on immunity to prevent or treat disease. Specific examples of the medicament that acts on immunity to prevent or treat disease include prophylactic vaccines against infections (for example, prophylactic vaccines against infections such as diphtheria, tetanus, and pertussis), anti-virus agents (for example, influenza vaccine, hepatitis B vaccine, interferon α preparations, interferon β preparations, telaprevir, ribavirin, simeprevir, sofosbuvir, ledipasvir-sofosbuvir combination preparations, vidarabine, aciclovir, ganciclovir, valganciclovir, nucleoside analog reverse transcriptase inhibitors (NRTI; for example, AZT (zidovudine), ddI (didanosine), ddC (zalcitabine), d4T (stavudine), and 3TC (lamibudine)), non-nucleoside reverse transcriptase inhibitors (NNRTI; for example, nevirapine and delavirdine), protease inhibitors (saquinavir, ritonavir, indinavir, and nelfinavir), and anti-tumor immune response inducers (for example, immune checkpoint molecule regulators, and cancer vaccines (for example, sipuleucel T). In this respect, another aspect of the present invention relates to a pharmaceutical composition containing an acyl thiourea compound represented by general formula (I) or a salt thereof for potentiating effects of a medicament that acts on immunity to prevent or treat disease, and an acyl thiourea compound represented by general formula (I) or a salt thereof for potentiating effects of a medicament that acts on immunity to prevent or treat disease, and to a method for potentiating effects of a medicament that acts on immunity to prevent or treat disease, wherein the method includes administering the medicament and an effective amount of an acyl thiourea compound represented by general formula (I) or a salt thereof to the patient.

In the present invention, from the viewpoint of potentiating the antitumor effects of an immune checkpoint molecule regulator or enhancing the immunostimulatory effects with an acyl thiourea compound represented by general formula (I) or a salt thereof, the dose of an acyl thiourea compound represented by general formula (I) or a salt thereof per day of administration is preferably 25 to 100%, more preferably 50 to 100%, even more preferably 60 to 100%, particularly preferably 80 to 100%, most preferably 100% of the recommended dose of when the acyl thiourea compound represented by general formula (I) or a salt thereof is administered alone. The recommended dose in humans is preferably 100 to 1,200 mg/body/day, more preferably 200 to 800 mg/body/day, particularly preferably 200 to 650 mg/body/day.

In the present invention, from the viewpoint of potentiating the antitumor effects of an immune checkpoint molecule regulator or enhancing the immunostimulatory effect with the acyl thiourea compounds represented by compound 1 or salts thereof, the dose of the acyl thiourea compounds represented by compound 1 or salts thereof per day of administration is preferably 25 to 100%, more preferably 50 to 100%, even more preferably 60 to 100%, particularly preferably 80 to 100%, most preferably 100% of the recommended dose of when the acyl thiourea compounds represented by compound 1 or salts thereof is administered alone. The recommended dose in humans is preferably 100 to 1,200 mg/body/day, more preferably 200 to 800 mg/body/day, particularly preferably 200 to 650 mg/body/day.

In the present invention, from the viewpoint of potentiating the antitumor effects of an immune checkpoint molecule regulator with acyl thiourea compounds represented by general formula (I) or a salt thereof, the dose of the immune checkpoint molecule regulator per day of administration is preferably 30 to 100%, more preferably 50 to 100%, particularly preferably 100% of the recommended dose of when the immune checkpoint molecule regulator is administered alone.

In the present invention, from the viewpoint of potentiating the antitumor effects of an immune checkpoint molecule regulator with the acyl thiourea compounds represented by compound 1 or salts thereof, the dose of the immune checkpoint molecule regulator per day of administration is preferably 10 to 50%, more preferably 20 to 40%, particularly preferably 33% of the recommended dose of when the immune checkpoint molecule regulator is administered alone.

Specifically, with respect to the recommended dose for administration of nivolumab alone, the approved dose for administration of nivolumab alone is 2 mg/kg (body weight) per administration or 3 mg/kg (body weight) per administration in Japan. Accordingly, in the present invention, the dose of nivolumab per day of administration is preferably 0.3 to 3 mg/kg (body weight) per administration, more preferably 1 to 3 mg/kg (body weight) per administration, even more preferably 2 mg/kg (body weight) per administration or 3 mg/kg (body weight) per administration.

With respect to the recommended dose for administration of pembrolizumab alone, the approved dose for administration of pembrolizumab alone is 2 mg/kg (body weight) per administration or 200 mg per administration in Japan. Accordingly, in the present invention, the dose of pembrolizumab per day of administration is preferably 0.2 to 2 mg/kg (body weight) per administration or 20 to 200 mg per administration, more preferably 1 to 2 mg/kg (body weight) per administration or 100 to 200 mg per administration, even more preferably 2 mg/kg (body weight) per administration or 200 mg per administration.

With respect to the recommended dose for administration of atezolizumab alone, the approved dose for administration of atezolizumab alone is 1,200 mg per administration in the United States. Accordingly, in the present invention, the dose of atezolizumab per day of administration is preferably 120 to 1,200 mg per administration, more preferably 600 to 1,200 mg per administration, even more preferably 1,200 mg per administration.

In the present invention, from the viewpoint of the effect of acyl thiourea compounds represented by general formula (I) or salts thereof potentiating effects of a medicament that acts on immunity to prevent or treat disease, the dose for administration of a medicament that acts on immunity to prevent or treat disease per day is preferably 50 to 100%, more preferably 100% of the recommended dose of when the medicament that acts on immunity to prevent or treat disease is administered alone.

With respect to the recommended dose for administration of ipilimumab alone, the approved dose for administration of ipilimumab alone is 3 mg/kg (body weight) per administration in Japan. Accordingly, in the present invention, the dose of ipilimumab per day of administration is preferably 0.3 to 3 mg/kg (body weight) per administration, 1.5 to 3 mg/kg (body weight) per administration, even more preferably 3 mg/kg (body weight) per administration.

As used herein, "recommended dose" is a dose that has been determined through experiments such as in clinical trials to be a quantity that brings about the maximum therapeutic effect while being safe to use without causing serious side effects. Specifically, the recommended dose may be any of the doses approved, recommended, or advised by public institutions or organizations such as the Japan Pharmaceuticals and Medical Devices Agency (PMDA), the US Food and Drug Administration (FDA), and the European Medicines Agency (EMA), and that are indicated in instructions such as package inserts, interview forms, and treatment guidelines. Preferably, the recommended dose is a dose approved by any of PMDA, FDA, and EMA.

When using nivolumab as an immune checkpoint molecule regulator, the dose of a compound represented by general formula (I) or a pharmaceutically acceptable salt thereof may be preferably 0.6 to 10.8 mg, more preferably 0.6 to 10 mg, even more preferably 1.1 to 6.7 mg, particularly preferably 1.1 to 5.4 mg with respect to 1 mg of nivolumab.

When using pembrolizumab as an immune checkpoint molecule regulator, the dose of a compound represented by general formula (I) or a pharmaceutically acceptable salt thereof may be preferably 0.5 to 10 mg, more preferably 0.5 to 9.75 mg, even more preferably 1.0 to 6.7 mg, particularly preferably 1.1 to 5.4 mg with respect to 1 mg of pembrolizumab.

When using atezolizumab as an immune checkpoint molecule regulator, the dose of a compound represented by general formula (I) or a pharmaceutically acceptable salt thereof may be preferably 0.08 to 1.62 mg, more preferably 0.08 to 1 mg, even more preferably 0.17 to 0.67 mg, particularly preferably 0.17 to 0.54 mg with respect to 1 mg of atezolizumab.

When using ipilimumab as an immune checkpoint molecule regulator, the dose of a compound represented by general formula (I) or a pharmaceutically acceptable salt thereof may be preferably 0.6 to 10.8 mg, more preferably 0.6 to 6.7 mg, even more preferably 1.1 to 4.4 mg, particularly preferably 1.1 to 3.6 mg with respect to 1 mg of ipilimumab.

The dosing schedule of the antitumor agent of the present invention may be appropriately selected according to factors such as type of cancer, and stage of disease.

In the case of an acyl thiourea compound represented by general formula (I) or salts thereof, the antitumor agent is administered preferably daily, or in a cycle with 5 days of continuous administration followed by a 2-day rest.

When the immune checkpoint molecule regulator is nivolumab, the antitumor agent is administered preferably twice a week, once a week, or once in 2 to 3 weeks. In the case of pembrolizumab, the antitumor agent is administered preferably twice a week, once a week, or once in 3 weeks. In the case of atezolizumab, the antitumor agent is administered preferably twice a week, once a week, or once in 3 weeks. In the case of ipilimumab, the antitumor agent is administered preferably twice a week, once a week, or once in 3 weeks.

The number of doses per day of the antitumor agent of the present invention may be appropriately selected according to factors such as type of cancer, and stage of disease.

The antitumor agent is administered preferably once daily, regardless of whether the immune checkpoint molecule regulator is nivolumab, pembrolizumab, atezolizumab, or ipilimumab.

The order of administration of the acyl thiourea compound represented by general formula (I) or a salt thereof of the present invention, and the immune checkpoint molecule regulator may be appropriately selected according to factors such as type of cancer, and stage of disease, and these may be administered in this order or in reversed order, or may be administered simultaneously.

The dosing interval of the acyl thiourea compound represented by general formula (I) or a salt thereof of the present invention, and the immune checkpoint molecule regulator may be appropriately selected according to factors such as type of cancer, and stage of disease. Specifically, these may be administered on the same day or with an interval of at most 2 weeks. Preferably, the compounds are administered on the same day or with an interval of at most 1 week, more preferably on the same day or with an interval of 2 days.

The target tumor in the present invention is not particularly limited, as long as enhanced antitumor effects can be produced in the tumor. Preferably, the target tumors are tumors in which acyl thiourea compounds represented by general formula (I) or salts thereof can produce antitumor effects, more preferably malignant tumors involving c-Met, and tumors with high numbers of tumor-infiltrating macrophages.

In the case of malignant tumors, specific examples of target cancers in the present invention include head and neck cancer, esophageal cancer, stomach cancer, colon cancer, rectal cancer, liver cancer, gallbladder-bile duct cancer, biliary tract cancer, pancreas cancer, colon cancer, urethral cancer, lung cancer, breast cancer, ovarian cancer, cervical cancer, endometrial cancer, kidney cancer, bladder cancer, prostate cancer, testicular tumor, osteosarcoma and soft tissue sarcoma, leukemia, malignant lymphoma, multiple myeloma, skin cancer, brain tumor, and mesothelioma.

The target cancers in the present invention are preferably melanoma, kidney cancer, lung cancer, head and neck cancer, Hodgkin's lymphoma, bladder cancer, colon cancer, liver cancer, stomach cancer, osteosarcoma and soft tissue sarcoma, breast cancer, prostate cancer, esophageal cancer, ovarian cancer, glioblastoma, mesothelioma, multiple myeloma, and urethral cancer, more preferably melanoma, kidney cancer, lung cancer, head and neck cancer, Hodgkin's lymphoma, bladder cancer, colon cancer, liver cancer, stomach cancer, osteosarcoma and soft tissue sarcoma, breast cancer, and prostate cancer, particularly preferably colon cancer, breast cancer, lung cancer, melanoma, osteosarcoma and soft tissue sarcoma, most preferably colon cancer and breast cancer.

An acyl thiourea compound represented by general formula (I) or a salt thereof, an immune checkpoint molecule regulator, and a medicament that acts on immunity to prevent or treat disease may be prepared in separate forms containing the respective active components, (kit preparation), or may be prepared in a single form (compounding agent), depending on the dosage forms and the dosing schedules of the active components. In the case of a kit preparation, the agents may be produced and sold as a single package suited for coadministration, or may be produced and sold as separate packages.

The dosage form of the antitumor agent of the present invention is not particularly limited, and may be appropriately selected according to the intended treatment. Specific examples of possible dosage forms include oral agents (e.g., tablets, coated tablets, powders, granules, capsule formulations, and liquid formulations), injections, suppositories, patches, and ointments.

In the case of an acyl thiourea compound represented by general formula (I) or a salt thereof, the antitumor agent is preferably an oral agent.

In the case of an immune checkpoint molecule regulator, the antitumor agent may have any of the dosage forms exemplified above. Specifically, in the case of an anti-PD-1 antibody, an anti-PD-L1 antibody, or an anti-CTLA-4 antibody, the preferred dosage form is injection.

The antitumor agent, an immunostimulant, and a medicament that acts on immunity to prevent or treat disease of the present invention may be prepared using a pharmaceutically acceptable carrier, using a common known method, depending on the dosage form, regardless of whether these are an acyl thiourea compound represented by general formula (I) or a salt thereof, an immune checkpoint molecule regulator, or a medicament that acts on immunity to prevent or treat disease. The carrier may be any of common carriers used for typical medicinal agents. Examples of such carriers include excipients, binders, disintegrants, lubricants, diluents, solubilizing agents, suspending agents, tonicity agents, pH adjusters, buffers, stabilizers, colorants, flavoring agents, and odor improving agents.

The present invention also relates to an antitumor effect potentiator containing an acyl thiourea compound represented by general formula (I) or a salt thereof for potentiation of antitumor effects of an immune checkpoint molecule regulator in a cancer patient. The antitumor effect potentiator is prepared in any of the forms listed above for the antitumor agent.

The present invention also relates to an antitumor effect potentiator containing an immune checkpoint molecule regulator for potentiation of antitumor effects of an acyl thiourea compound represented by general formula (I) or a salt thereof in a cancer patient. The antitumor effect potentiator is prepared in any of the forms listed above for the antitumor agent.

The present invention also relates to an immunostimulant containing an acyl thiourea compound represented by general formula (I) or a salt thereof for potentiation of effects of a medicament that acts on immunity to prevent or treat medical conditions in a patient having a disease ameliorable by immunostimulation. The immunostimulant is prepared in any of the forms listed above for the immunostimulant.

The present invention also relates to an antitumor agent containing an acyl thiourea compound represented by general formula (I) or a salt thereof for treatment of a cancer patient to whom an immune checkpoint molecule regulator is administered. The antitumor agent is prepared in any of the forms listed above.

The present invention also relates to an antitumor agent containing an immune checkpoint molecule regulator for treatment of a cancer patient to whom an acyl thiourea compound represented by general formula (I) or a salt thereof is administered. The antitumor agent is prepared in any of the forms listed above.

As used herein, "treatment" is inclusive of postoperative adjuvant chemotherapy performed to prevent recurrence after surgical removal of tumor, and a preoperative adjuvant chemotherapy performed before surgical removal of tumor.

The present invention also relates to an immunostimulant containing an acyl thiourea compound represented by general formula (I) or a salt thereof for treatment of a patient having a disease ameliorable by immunostimulation, the patient to whom a medicament that acts on immunity to prevent or treat disease is administered. The immunostimulant is prepared in any of the forms listed above.

The present invention also relates to an antitumor agent containing an acyl thiourea compound represented by general formula (I) or a salt thereof, wherein the antitumor agent is used with an immune checkpoint molecule regulator for a cancer patient in combination. The antitumor agent is prepared in any of the forms listed above.

The present invention also relates to an antitumor agent containing an immune checkpoint molecule regulator, wherein the antitumor agent is used with an acyl thiourea compound represented by general formula (I) or a salt thereof for a cancer patient in combination. The antitumor agent is prepared in any of the forms listed above.

The present invention also relates to an immunostimulant containing an acyl thiourea compound represented by general formula (I) or a salt thereof, wherein the immunostimulant is used with a medicament that acts on immunity to prevent or treat disease in a patient having a disease ameliorable by immunostimulation in combination. The immunostimulant is prepared in any of the forms listed above.

The present invention also relates to a kit preparation containing:
  an antitumor agent containing an acyl thiourea compound represented by general formula (I) or a salt thereof; and
  an instruction manual containing instructions for coadministration of an acyl thiourea compound represented by general formula (I) or a salt thereof, and an immune checkpoint molecule regulator to a cancer patient.

Here, "instruction manual" may contain instructions indicating the doses specified above, and may or may not be legally binding. Preferably, the instruction manual specifies the foregoing doses as recommended doses. Specific examples of such instruction manuals include package inserts and pamphlets. The kit preparation containing an instruction manual may be such that the instruction manual is printed or attached to the package of the kit preparation, or the instruction manual may be enclosed in the package of the kit preparation, together with the antitumor agent or immunostimulant.

The present invention also relates to a kit preparation containing:
  an immunostimulant containing an acyl thiourea compound represented by general formula (I) or a salt thereof; and
  an instruction manual containing instructions for coadministration of an acyl thiourea compound represented by general formula (I) or a salt thereof, and a medicament that acts on immunity to prevent or treat disease to a patient having a disease ameliorable by immunostimulation.

The following describes the present invention in greater detail by way of Examples. It is to be noted, however, that the present invention is in no way limited by the following Examples, and various modifications may be made by a person of ordinary skill in the art without departing from the technical idea of the invention disclosed herein.

EXAMPLE 1

An experiment was conducted with mouse MC38 tumor model. Tumor cells were cultured in vitro and transplanted subcutaneously into male mice, six weeks of age, in the right chest region, followed by daily administration of compound 1 and a control antibody. In continuous administration, the preferred minimum dose of compound 1 that produces the maximum efficacy in the mouse was found to be 50 mg/kg when orally administered once daily for 21 days. This dose (oral continuous administration of 50 mg/kg for 21 days, q.d.) is equivalent to the recommended dose of compound 1 in humans when administered alone.

Example 1 Combined Effects (Antitumor Effects) of Methanesulfonic Acid Salt of Compound 1 and Anti-Mouse PD-1 Antibody in Colon Cancer Cell Transplant Model MC38, a mouse colon cancer cell line, was provided by Dr. Yoshihiro Hayakawa (University of Toyama, Toyama, Japan). MC38 was cultured in RPMI 1640 medium containing 10% fetal bovine serum (FBS). MC38 was subcultured in a 37° C., 5% $CO_2$ incubator in a 1:3 to 1:5 ratio, one to two times a week.

A cell suspension as a suspension of MC38 cells in a 1:1 mixture of phosphate-buffered saline (PBS) and extracellular matrix component Matrigel was prepared, and the suspension, containing $1 \times 10^6$ cells/0.1 mL, was transplanted subcutaneously into a C57BL/6NCrl mouse (Charles River Laboratories Japan Inc.), six weeks of age, in an area around the right last rib.

After transplantation, a tumor was allowed to grow until it had a tumor volume (TV) of 100 to 200 $mm^3$. The tumor size was measured by measuring the major axis and minor axis of the tumor with a digimatic caliper, and TV was calculated using the following formula.

$$TV\ (mm^3) = \text{major axis (mm)} \times \text{minor axis (mm)} \times \text{minor axis (mm)}/2$$

The animals were divided into groups of 10 using a stratified random grouping method, using TV as an index. The day the grouping was made (N=10) was designated as Day 1.

An electronic balance designed for animals was used for body weight measurement. A percentage of body weight change (BWCn) on day n was calculated from the body weight on day 1 (BW1) and the body weight (BWn) on day n using the following formula.

Percentage of body weight change BWCn (%)=
($BWn-BW1$)/$BW1$×100

A methanesulfonic acid salt of compound 1 was pulverized with an agate mortar, and was prepared into a solution having a concentration of 5 mg/mL as its free form, using a solvent. The compound was then dissolved by sonication to prepare a 50 mg/kg dosing solution. The dosing solution was diluted with solvent to prepare a 25 mg/kg dosing solution, and a 12.5 mg/kg dosing solution. These dosing solutions were orally administered as compound 1, once daily in a dose of 12.5 mg/kg/day, 25 mg/kg/day, or 50 mg/kg/day, continuously for 21 days.

Anti-mouse PD-1 antibody (anti-mPD-1 Ab) was prepared by diluting Anti-Mouse CD279 (PD-1) Functional Grade Purified (Clone: RMP-1-14, Affymetrix) with PBS in such a manner that the antibody had a predetermined concentration immediately before administration. The anti-mouse PD-1 antibody was intraperitoneally administered in a dose of 0.05 mg/body on the first day (Day 1) of administration and on the 8th day since administration was started.

The medicinal agents shown in Table 1 were administered in the schedules, doses, and dosage forms shown in Table 1 (administered group No. 1 to No. 8). The results are presented in FIG. 1 and Table 1.

A Dunnett's test (significance level 0.05) was conducted to analyze Day 22 TV for each group. The group with sole administration of anti-mouse PD-1 antibody (No. 2), the groups with sole administration of different doses of compound 1 (No. 3 to No. 5), and the groups with coadministration of different doses of compound 1+anti-mouse PD-1 antibody (No. 6 to No. 8) all had significantly smaller TVs than control group (No. 1), showing antitumor effects. In a Student's t test (significance level 0.05), the compound 1+anti-mouse PD-1 antibody coadministered groups had significantly smaller TVs, and showed stronger antitumor effects than the groups with sole administration of compound 1 or the group with sole administration of anti-mouse PD-1 antibody, regardless of the dose of compound 1.

The mean $BWC_{22}$ of the coadministered groups were not notably different from the groups with sole administration of compound 1 or the group with sole administration of anti-mouse PD-1 antibody, and the coadministration did not involve increase of toxicity, regardless of the dose of compound 1.

The results showed that coadministration of compound 1 or a salt thereof and the anti-PD-1 antibody produces a significantly higher antitumor effect than when these are administered alone.

Example 2 Combined Effects (Effects on Tumor-Associated Macrophage) of Methanesulfonic Acid Salt of Compound 1 and Anti-Mouse PD-1 Antibody in Colon Cancer Cell Transplant Model MC38, a mouse colon cancer cell line, was provided by Dr. Yoshihiro Hayakawa (University of Toyama, Toyama, Japan). MC38 was cultured in RPMI 1640 medium contain-

TABLE 1

| Group | | | | | TV, DAY 22 (mm$^3$) | |
|---|---|---|---|---|---|---|
| No. | Medicinal agent | Schedule Day | Dose | Administration route | BWC$_{22}$ (%) MEAN ± S.E. | MEAN ± S.E. | Result of significant difference test |
| 1 | Solvent/PBS | q.d. 1-21 1, 8 | — | p.o./i.p. | -2.7 ± 1.9 | 2447 ± 154 | — |
| 2 | Solvent/ Anti-mouse PD-1 antibody | q.d. 1-21 1, 8 | —/0.05 mg/body | p.o./i.p. | 4.3 ± 1.0 | 1217 ± 250 | *, #, *, † |
| 3 | Compound 1/ PBS | q.d. 1-21 1, 8 | 12.5 mg/ kg/— | p.o./i.p. | 6.1 + 0.7 | 1007 ± 161 | *, # |
| 4 | Compound 1/ PBS | q.d. 1-21 1, 8 | 25 mg/ kg/— | p.o./i.p. | 5.0 ± 0.9 | 763 ± 50 | *, * |
| 5 | Compound 1/ PBS | q.d. 1-21 1, 8 | 50 mg/ kg/— | p.o./i.p. | -0.3 ± 0.9 | 437 ± 62 | *, † |
| 6 | Compound 1/ Anti-mouse PD-1 antibody | q.d. 1-21 1, 8 | 12.5 mg/ kg/0.05 mg/body | p.o./i.p. | 2.2 ± 0.6 | 409 ± 82 | * |
| 7 | Compound 1/ Anti-mouse PD-1 antibody | q.d. 1-21 1, 8 | 25 mg kg/0.05 mg/body | p.o./i.p. | 0.7 ± 0.8 | 225 ± 53 | * |
| 8 | Compound 1/ Anti-mouse PD-1 antibody | q.d. 1-21 1, 8 | 50 mg/ kg/0.05 mg/body | p.o./i.p. | 0.1 ± 1.0 | 205 ± 43 | * | q.d.: Once daily
p.o.: Oral administration
i.p.: Intraperitoneal administration
* p < 0.05 with Dunnett's test vs Group No. 1
: p < 0.05 with Student t test vs Group No. 6
* p < 0.05 with Student t test vs Group No. 7
†: p < 0.05 with Student t test vs Group No. 8 ing 10% FBS. MC38 was subcultured in a 37° C., 5% $CO_2$ incubator in a 1:3 to 1:5 ratio, one to two times a week.

A cell suspension of MC38 cells containing $2\times10^6$ cells/ 0.1 mL, was transplanted subcutaneously into a C57BL/ 6NJJcl mouse (CLEA Japan, Inc.), six weeks of age, in an area around the right last rib.

After transplantation, a tumor was allowed to grow until it had a TV of 50 to 300 $mm^3$. The tumor size was measured by measuring the major axis and minor axis of the tumor with a digimatic caliper, and TV was calculated using the following formula.

$TV$ ($mm^3$)=major axis (mm)×minor axis (mm)×minor axis (mm)/2

The animals were divided into groups of 5 using a stratified random grouping method, using TV as an index. The day the grouping was made (N=5) was designated as Day 1.

A methanesulfonic acid salt of compound 1 was pulverized with an agate mortar, and was prepared into a solution having a concentration of 2.5 mg/mL as its free form, using a solvent. The compound was then dissolved by sonication to prepare a 25 mg/kg dosing solution.

The dosing solution was orally administered as compound 1, once daily in a dose of 25 mg/kg/day, continuously for 9 days.

Anti-mouse PD-1 antibody (anti-mPD-1 Ab) was prepared by diluting Anti-Mouse CD279 (PD-1) Functional Grade Purified (Clone: RMP-1-14, Affymetrix) with PBS in such a manner that the antibody had a predetermined concentration immediately before administration. The anti-mouse PD-1 antibody was intraperitoneally administered in a dose of 0.05 mg/body on the first day (Day 1) of administration.

The tumor was collected on the 10th day (Day 10) since administration was started, and a tumor suspension was prepared using a digestive enzyme treatment method. The tumor suspension was then reacted with magnetic beads having immobilized thereon an antibody (anti-mouse CD45 antibody) against CD45 (leukocyte marker)—an antigen commonly expressed on leukocytes, and was passed through a magnetic column to isolate tumor infiltrated leukocytes (TILs). The isolated TILs were reacted with fluorescence-labeled anti-CD45 antibody, anti-CD90.2 (T cell marker) antibody, anti-CD11b (myeloid leukocyte marker) antibody, anti-Ly-6G (granulocytic bone marrow-derived suppressor cell marker) antibody, anti-Ly-6C (monocytic bone marrow-derived suppressor cell marker) antibody, and anti-F4/80 (macrophage marker) antibody, and the fraction of tumor-associated macrophage in TIL was calculated by fluorescence flow cytometry. The definition of tumor-associated macrophage, and the method used to calculate the fraction of tumor-associated macrophage in TIL are as follows.

Tumor-associated macrophage: CD45 positive, CD90.2 negative, CD11b positive, Ly6-G negative, Ly-6C negative, and F4/80 positive Fraction of tumor-associated macrophage (%)=Number of tumor-associated macrophages÷Number of CD45 positive cells×100

The medicinal agents shown in Table 2 were administered in the schedules, doses, and dosage forms shown in Table 2 (administered group No. 1 to No. 4). The results are also presented in Table 2.

TABLE 2

| Group | | Schedule | | Administration | Fraction of tumor-associated macrophage (%) | |
|---|---|---|---|---|---|---|
| No. | Medicinal agent | Day | Dose | route | MEAN ± S.E. | Result of significance difference test |
| 1 | Untreated | — | — | — | 25.9 ± 3.5 | — |
| 2 | Anti-mouse PD-1 antibody | q.d. 1 | 0.05 mg/body | i.p. | 19.1 ± 3.3 | n.s. |
| 3 | Compound 1 | q.d. 1-9 | 25 mg/kg | p.o. | 8.2 ± 2.3 | * |
| 4 | Compound 1/ Anti-mouse PD-1 antibody | q.d. 1-9/1 | 25 mg/ kg/0.05 mg/body | p.o./i.p. | 11.7 ± 1.8 | * | q.d.: Once daily
p.o.: Oral administration
i.p.: Intraperitoneal administration
n.s.: $p > 0.05$ with Dunnett's test vs Group No. 1
* $p < 0.05$ with Dunnett's test vs Group No. 1

A Dunnett's test (significance level 0.05) was conducted to analyze the fraction of tumor-associated macrophage for each group. The group with sole administration of compound 1 (No. 3), and the group with coadministration of compound 1+anti-mouse PD-1 antibody (No. 4) had significantly smaller fractions of tumor-associated macrophage than control group (No. 1), showing a tumor-associated macrophage suppressing effect. The group with sole administration of anti-mouse PD-1 antibody (No. 2) did not show a significant suppressing effect against tumor-associated macrophage.

These results confirmed that compound 1 or salts thereof have immunostimulatory effects, and produce the effects even when compound 1 or salts thereof is used with anti-PD-1 antibody in colon cancer in combination.

Example 3 Combined Effects of Three Agents (Antitumor Effects) of Methanesulfonic Acid Salt of Compound 1, Anti-Mouse PD-1 Antibody, and Anti-Mouse CTLA-4 Antibody in Breast Cancer Cell Transplant Model EMT6, a mouse breast cancer cell line, was obtained from American Type Culture Collection (ATCC). EMT6 was cultured in Waymouth's MB752/1 medium containing 15% PBS. EMT6 was subcultured in a 37° C., 5% $CO_2$ incubator in a 1:3 to 1:5 ratio, one to two times a week.

A cell suspension as a suspension of EMT6 cells in a 1:1 mixture of PBS and extracellular matrix component Matrigel was prepared, and the suspension, containing $1\times10^4$ cells/0.1 mL, was transplanted subcutaneously into a BALB/c mouse (Charles River Laboratories Japan Inc.), six weeks of age, in an area around the right last rib.

After transplantation, a tumor was allowed to grow until it had a tumor volume (TV) of 50 to 200 mm$^3$. The tumor size was measured by measuring the major axis and minor axis of the tumor with a digimatic caliper, and TV was calculated using the following formula.

TV (mm$^3$)=major axis (mm)×minor axis (mm)×minor axis (mm)/2

(CD152) (Clone: 9H10, Bio X Cell) with PBS in such a manner that the antibody had a predetermined concentration immediately before administration. The anti-mouse CTLA-4 antibody was intraperitoneally administered in a dose of 0.5 mg/body on the first day (Day 1) of administration, and after 4 days (Day 4), 8 days (Day 8), and 11 days (Day 11) from administration.

Figure 2:
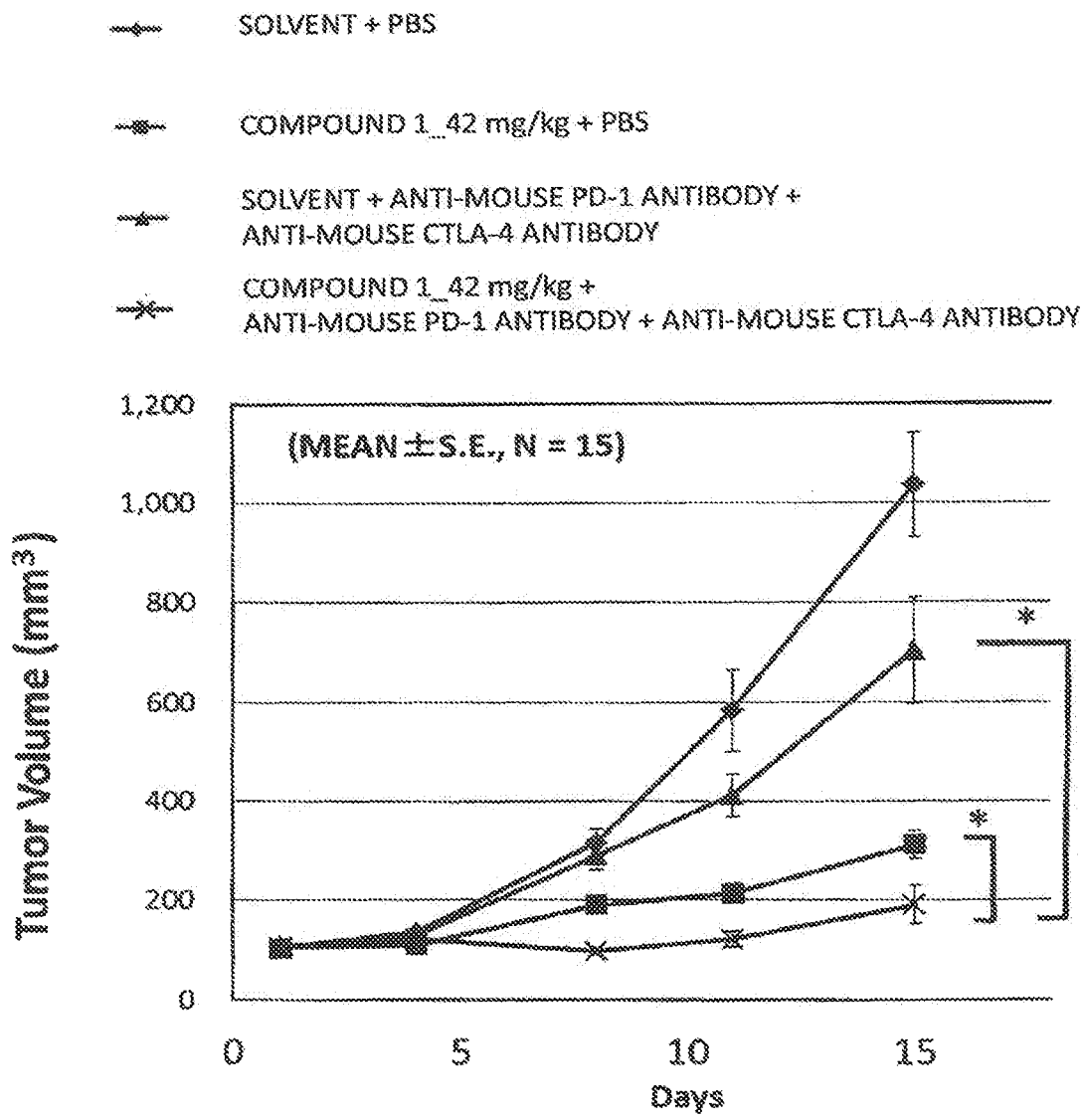
FIG. 2 represents a graph showing the combined effect of three agents, compound 1, anti-mouse PD-1 antibody and anti-mouse CTLA-4 antibody in a mouse model transplanted with mouse breast cancer cell line EMT6.

The medicinal agents shown in Table 3 were administered in the schedules, doses, and dosage forms shown in Table 3 (administered group No. 1 to No. 4). The results are presented in FIG. 2 and Table 3.

TABLE 3

| Group | | | Schedule | Administration | BWC$_{15}$ (%) | TV, DAY 15 (mm$^3$) | Result of significant |
|---|---|---|---|---|---|---|---|
| No. | Medicinal agent | Dose | (Day) | route | MEAN ± S.E. | MEAN ± S.E. | difference test |
| 1 | Solvent | — | q.d. 1-14 | p.o. | 7.4 ± 1.4 | 1037 ± 105 | — |
|   | PBS | — | q.d. 1, 4, 8, 11 | i.p. | | | |
| 2 | Compound 1 | 42 mg/kg | q.d. 1-14 | p.o. | 3.2 ± 1.0 | 312 ± 29 | *, # |
|   | PBS | — | q.d. 1, 4, 8, 11 | i.p. | | | |
| 3 | Solvent | — | q.d. 1-14 | p.o. | 9.4 ± 1.1 | 705 + 106 | *, # |
|   | Anti-mouse PD-1 antibody | 0.1 mg/body | q.d. 1, 4, 8, 11 | i.p. | | | |
|   | Anti-mouse CTLA-4 antibody | 0.5 mg/body | q.d. 1, 4, 8, 11 | i.p. | | | |
| 4 | Compound 1 | 42 mg/kg | q.d. 1-14 | p.o. | 2.4 ± 1.0 | 191 ± 38 | |
|   | Anti-mouse PD-1 antibody | 0.1 mg/body | q.d. 1, 4, 8, 11 | i.p. | | | |
|   | Anti-mouse CTLA-4 antibody | 0.5 mg/body | q.d. 1, 4, 8, 11 | i.p. | | | | q.d.: Once daily
p.o.: Oral administration
i.p.: Intraperitoneal administration
* $p < 0.05$ with Dunnett's test vs Group No. 1
: $p < 0.05$ with Student t test vs Group No. 4

The animals were divided into groups of 15 using a stratified random grouping method, using TV as an index. The day the grouping was made (N=15) was designated as Day 1.

An electronic balance designed for animals was used for body weight measurement. A percentage of body weight change (BWCn) on day n was calculated in the same manner as in Example 1.

A methanesulfonic acid salt of compound 1 was pulverized with an agate mortar, and was prepared into a solution having a concentration of 4.2 mg/mL as its free form, using a solvent. The compound was then dissolved by sonication to prepare a 42 mg/kg dosing solution. The dosing solution was orally administered as compound 1, once daily in a dose of 42 mg/kg/day, continuously for 14 days.

Anti-mouse PD-1 antibody (anti-mPD-1 Ab) was prepared by diluting Anti-Mouse CD279 (PD-1) Functional Grade Purified (Clone: RMP-1-14, Affymetrix) with PBS in such a manner that the antibody had a predetermined concentration immediately before administration. The anti-mouse PD-1 antibody was intraperitoneally administered in a dose of 0.1 mg/body on the first day (Day 1) of administration, and on the 4th day (Day 4), the 8th day (Day 8), and the 11th day (Day 11) since administration was started.

Anti-mouse CTLA-4 antibody (anti-mCTLA-4 Ab) was prepared by diluting In Vivo MAb Anti-Mouse CTLA-4

A Dunnett's test (significance level 0.05) was conducted to analyze Day 15 TV for each group. The group with coadministration of anti-mouse PD-1 antibody and anti-CTLA-4 antibody (No. 3), the group with sole administration of compound 1 (No. 2), and the group with three agents coadministration of compound 1+anti-mouse PD-1 antibody+anti-mouse CTLA-4 antibody (No. 4) all had significantly smaller TVs than control group (No. 1), showing antitumor effects. In a Student's t test (significance level 0.05), the group with three agents coadministration of the compound 1+anti-mouse PD-1 antibody+anti-mouse CTLA-4 antibody had a significantly smaller TV, and showed stronger antitumor effects than the group with sole administration of compound 1 or the group with coadministration of anti-mouse PD-1 antibody+anti-mouse CTLA-4 antibody.

The mean BWC$_{15}$ of the group with three agents coadministration was not notably different from the group with sole administration of compound 1 or the group with coadministration of the anti-mouse PD-1 antibody+anti-mouse CTLA-4. And this showed that the group with three agents coadministration did not involve increase of toxicity.

The results showed that coadministration of compound 1 or salts thereof, anti-PD-1 antibody, and anti-CTLA-4 antibody produces a significantly higher antitumor effect than when these are administered alone.

Example 4 Effects (Effects on Tumor-Associated Macrophage) of Methanesulfonic Acid Salt of Compound 1, and Effects of Two Agents of Coadministration of Anti-Mouse PD-1 Antibody and Anti-Mouse CTLA-4 Antibody in Breast Cancer Cell Transplant Model EMT6, a mouse breast cancer cell line, was obtained from ATCC. EMT6 was cultured in Waymouth's MB752/1 medium containing 15% FBS. EMT6 was subcultured in a 37° C., 5% $CO_2$ incubator in a 1:3 to 1:5 ratio, one to two times a week.

A cell suspension as a suspension of EMT6 cells in a 1:1 mixture of PBS and extracellular matrix component Matrigel was prepared, and the suspension, containing $1×10^4$ cells/0.1 mL, was transplanted subcutaneously into a BALB/c mouse (Charles River Laboratories Japan Inc.), six weeks of age, in an area around the right last rib.

After 4 days from transplantation, the animals were divided into groups of 5 using a stratified random grouping method, using body weight as an index. The day the grouping was made (N=5) was designated as Day 1.

A methanesulfonic acid salt of compound 1 was pulverized with an agate mortar, and was prepared into a solution having a concentration of 4.2 mg/mL as its free form, using a solvent. The compound was then dissolved by sonication to prepare a 42 mg/kg dosing solution. The dosing solution was orally administered as compound 1, once daily in a dose of 42 mg/kg/day, continuously for 6 days.

Anti-mouse PD-1 antibody (anti-mPD-1 Ab) was prepared by diluting Anti-Mouse CD279 (PD-1) Functional Grade Purified (Clone: RMP-1-14, Affymetrix) with PBS in such a manner that the antibody had a predetermined concentration immediately before administration. The anti-mouse PD-1 antibody was intraperitoneally administered in a dose of 0.1 mg/body on the first day (Day 1) of administration, and on the 4th days (Day 4) since administration was started.

Anti-mouse CTLA-4 antibody (anti-mCTLA-4 Ab) was prepared by diluting In Vivo MAb Anti-Mouse CTLA-4 (CD152) (Clone: 9H10, Bio X Cell) with PBS in such a manner that the antibody had a predetermined concentration immediately before administration. The anti-mouse CTLA-4 antibody was intraperitoneally administered in a dose of 0.5 mg/body on the first day (Day 1) of administration, and on the 4th day (Day 4) since administration was started.

The tumor was collected on the 7th day (Day 7) since administration was started, and a tumor suspension was prepared using a digestive enzyme treatment method. The tumor suspension was then reacted with magnetic beads having immobilized thereon an antibody (anti-mouse CD45 antibody) against CD45 which is commonly expressed on leukocytes, and was passed through a magnetic column to isolate TILs. The isolated TILs were reacted with fluorescence-labeled anti-CD45 antibody, anti-CD90.2 antibody, anti-CD11b antibody, anti-Ly-6G antibody, anti-Ly-6C antibody, and anti-F4/80 antibody, and the fraction of tumor-associated macrophage in TIL was calculated by fluorescence flow cytometry. The definition of tumor-associated macrophage, and the method used to calculate the fraction of tumor-associated macrophage in TIL are as follows.

Tumor-associated macrophage: CD45 positive, CD90.2 negative, CD11b positive, Ly6-G negative, Ly-6C negative, and F4/80 positive Fraction of tumor-associated macrophage (%)=Number of tumor-associated macrophages÷Number of CD45 positive cells×100

The medicinal agents shown in Table 4 were administered in the schedules, doses, and dosage forms shown in Table 4 (administered group No. 1 to No. 3). The results are also presented in Table 4.

TABLE 4

| Group | | Schedule | | Administration | Fraction of tumor-associated macrophage (%) | |
|---|---|---|---|---|---|---|
| No. | Medicinal agent | Day | Dose | route | MEAN ± S.E. | Result of significance difference test |
| 1 | Untreated | — | — | — | 41.4 ± 6.4 | — |
| 2 | Compound 1 | q.d.1-6 | 42 mg/kg | p.o. | 20.3 ± 4.8 | * |
| 3 | Anti-mouse PD-1 antibody/Anti-mouse CTLA-4 antibody | q.d.1-4/ q.d.1-4 | 0.1 mg/ body/0.5 mg/kg/body | i.p./i.p. | 35.7 ± 4.5 | n.s. | q.d.: Once daily
p.o.: Oral administration
i.p.: Intraperitoneal administration
n.s: p > 0.05 with Dunnett's test vs Group No. 1
* p < 0.05 with Dunnett's test vs Group No. 1

A Dunnett's test (significance level 0.05) was conducted to analyze the fraction of tumor-associated macrophage for each group. The group with sole administration of compound 1 (No. 2) had a significantly smaller fraction of tumor-associated macrophage than control group (No. 1), showing a tumor-associated macrophage suppressing effect. The group with coadministration of anti-mouse PD-1 antibody and anti-CTLA-4 antibody (No. 3) did not show a significant suppressing effect against tumor-associated macrophage.

These results indicated that compound 1 or salts thereof have immunostimulatory effects in breast cancer.

Example 5 Combined Effects (Antitumor Effects) of Methanesulfonic Acid Salt of Compound 1 and Anti-Mouse PD-1 Antibody in Breast Cancer Cell Transplant Model EMT6, a mouse breast cancer cell line, was obtained from American Type Culture Collection (ATCC). EMT6 was cultured in Waymouth's MB752/1 medium containing 15% FBS. EMT6 was subcultured in a 37° C., 5% $CO_2$ incubator in a 1:3 to 1:5 ratio, one to two times a week.

A cell suspension as a suspension of EMT6 cells in a 1:1 mixture of PBS and extracellular matrix component Matrigel was prepared, and the suspension, containing $1\times10^4$ cells/0.1 mL, was transplanted subcutaneously into a BALB/c mouse (Charles River Laboratories Japan Inc.), six weeks of age, in an area around the right last rib.

After transplantation, a tumor was allowed to grow until it had a TV of 50 to 200 $mm^3$. The tumor size was measured by measuring the major axis and minor axis of the tumor with a digimatic caliper, and TV was calculated using the following formula.

$$TV\ (mm^3) = major\ axis\ (mm) \times minor\ axis\ (mm) \times minor\ axis\ (mm)/2$$

The animals were divided into groups of 15 using a stratified random grouping method, using TV as an index. The first day of grouping (N=15) was designated as Day 1.

An electronic balance designed for animals was used for body weight measurement. A percentage of body weight change (BWCn) on day n was calculated in the same manner as in Example 1.

A methanesulfonic acid salt of compound 1 was pulverized with an agate mortar, and was prepared into a solution having a concentration of 4.2 mg/mL as its free form, using a solvent. The compound was then dissolved by sonication to prepare a 42 mg/kg dosing solution. The dosing solution was orally administered as compound 1, once daily in a dose of 42 mg/kg/day, continuously for 14 days.

Anti-mouse PD-1 antibody (anti-mPD-1 Ab) was prepared by diluting Anti-Mouse CD279 (PD-1) Functional Grade Purified (Clone: RMP-1-14, Affymetrix) with PBS in such a manner that the antibody had a predetermined concentration immediately before administration. The anti-mouse PD-1 antibody was intraperitoneally administered in a dose of 0.1 mg/body on the first day (Day 1) of administration, and on the 4th day (Day 4), the 8th day (Day 8), and the 11th day (Day 11) since administration was started.

Example 6 Combined Effects (Antitumor Effects) of Methanesulfonic Acid Salt of Compound 1 and Anti-Mouse CTLA-4 Antibody in Breast Cancer Cell Transplant Model EMT6, a mouse breast cancer cell line, was obtained from American Type Culture Collection (ATCC). EMT6 was cultured in Waymouth's MB752/1 medium containing 15% FBS. EMT6 was subcultured in a 37° C., 5% $CO_2$ incubator in a 1:3 to 1:5 ratio, one to two times a week.

A cell suspension as a suspension of EMT6 cells in a 1:1 mixture of PBS and extracellular matrix component Matrigel was prepared, and the suspension, containing $1\times10^4$ cells/0.1 mL, was transplanted subcutaneously into a BALB/c mouse (Charles River Laboratories Japan Inc.), six weeks of age, in an area around the right last rib.

After transplantation, a tumor was allowed to grow until it had a TV of 50 to 200 $mm^3$. The tumor size was measured by measuring the major axis and minor axis of the tumor with a digimatic caliper, and TV was calculated using the following formula.

$$TV\ (mm^3) = major\ axis\ (mm) \times minor\ axis\ (mm) \times minor\ axis\ (mm)/2$$

The animals were divided into groups of 15 using a stratified random grouping method, using TV as an index. The day the grouping was made (N=15) was designated as Day 1.

An electronic balance designed for animals was used for body weight measurement. A percentage of body weight change (BWCn) on day n was calculated in the same manner as in Example 1.

A methanesulfonic acid salt of compound 1 was pulverized with an agate mortar, and was prepared into a solution having a concentration of 4.2 mg/mL as its free form, using a solvent. The compound was then dissolved by sonication to prepare a 42 mg/kg dosing solution. The dosing solution was orally administered as compound 1, once daily in a dose of 42 mg/kg/day, continuously for 14 days.

Anti-mouse CTLA-4 antibody (anti-mCTLA-4 Ab) was prepared by diluting In Vivo MAb Anti-Mouse CTLA-4 (CD152) (Clone: 9H10, Bio X Cell) with PBS in such a manner that the antibody had a predetermined concentration immediately before administration. The anti-mouse CTLA-4 antibody was intraperitoneally administered in a dose of 0.5 mg/body on the first day (Day 1) of administration, and on the 4th day (Day 4), the 8th day (Day 8), and the 11th day (Day 11) since administration was started.

While the present invention has been described in detail and with reference to certain embodiments of the invention, it will be apparent to a skilled person that various changes and modifications may be made thereto without departing from the spirit and scope of the invention. This patent application is based on Japanese Patent Application Number 2017-173352 filed Sep. 8, 2017, the entire contents of which are hereby incorporated by reference.

The invention claimed is:

1. A method of treating a malignant tumor selected from the group consisting of melanoma, kidney cancer, lung cancer, head and neck cancer, Hodgkin's lymphoma, bladder cancer, colon cancer, liver cancer, stomach cancer, osteosarcoma and soft tissue sarcoma, breast cancer, and prostate cancer comprising coadministration 4-(2-fluoro-4-(3-(2-phenylacetyl) thioureido) phenoxy)-7-methoxy-N-methylquinoline-6-carboxamide or a salt thereof, and an immune checkpoint molecule regulator comprising an anti-PD-1 antibody.

2. The method of claim 1,
    wherein the anti-PD-1 antibody is at least one of nivolumab and pembrolizumab and the malignant tumor is colon cancer.

3. The method of claim 1,
    wherein a target cancer is at least one selected from, colon cancer, osteosarcoma and soft tissue sarcoma, and breast cancer.

4. The method of claim 1 wherein the anti-PD-1 antibody is at least one of nivolumab and pembrolizumab and a target cancer is at least one selected from, colon cancer, osteosarcoma and soft tissue sarcoma, and breast cancer.

* * * * *